United States Patent
Denu et al.

(10) Patent No.: US 12,390,447 B2
(45) Date of Patent: Aug. 19, 2025

(54) SIRTUIN 6 PROTEIN DEACYLASE (SIRT6) ACTIVATORS

(71) Applicant: Wisconsin Alumni Research Foundation, Madison, WI (US)

(72) Inventors: John Matthew Denu, Madison, WI (US); Weiping Tang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 694 days.

(21) Appl. No.: 17/782,577

(22) PCT Filed: Dec. 4, 2020

(86) PCT No.: PCT/US2020/063353
§ 371 (c)(1),
(2) Date: Jun. 3, 2022

(87) PCT Pub. No.: WO2021/113667
PCT Pub. Date: Jun. 10, 2021

(65) Prior Publication Data
US 2023/0064249 A1 Mar. 2, 2023

Related U.S. Application Data

(60) Provisional application No. 62/945,041, filed on Dec. 6, 2019.

(51) Int. Cl.
*A61K 31/4035* (2006.01)
*C07D 209/48* (2006.01)

(52) U.S. Cl.
CPC ........ *A61K 31/4035* (2013.01); *C07D 209/48* (2013.01)

(58) Field of Classification Search
CPC .......................... A61K 31/4035; C07D 209/48
See application file for complete search history.

(56) References Cited

FOREIGN PATENT DOCUMENTS

| WO | WO-2014/170873 A1 | 10/2014 |
| WO | WO-2014/197775 A1 | 12/2014 |

OTHER PUBLICATIONS

Office Action on CA 3,160,924 Dtd Feb. 28, 2024, 4 pages.
Office Action on EP 20828732.6 Dtd Apr. 2, 2024, 6 pages.
International Search Report and Written Opinion on PCT/US2020/063353 Dtd Feb. 12, 2021 (17 pages).
Klein, et al., "Mechanism of activation for the sirtuin 6 protein deacylase," J. Biol Chem. 295(5):1385-1399 (2020).
Sakai, et al., "Design, synthesis and structure-activity relationship studies of novel sirtuin 2 (SIRT2) inhibitors with a benzamide skeleton," Bioorganic & Medicinal Chemistry, 23(2):328-339 (2014).

*Primary Examiner* — Kamal A Saeed
(74) *Attorney, Agent, or Firm* — Foley & Lardner LLP

(57) ABSTRACT

The present disclosure provides compounds according to Formula I and pharmaceutically acceptable salts thereof, as well as compositions including such compounds and a pharmaceutically acceptable carrier or excipient. Further provided are methods of inactivating SIRT6 with compounds of Formula I as well as compounds of Formula III, $W^2$—$R^2$—Y—$R^3$, as described herein. In addition, the present technology provides methods of treatment using such compounds to lower LDL levels, lower triglyceride levels, and/or increase glucose tolerance in a subject, and/or to inhibit proliferation of ovarian, colorectal, hepatocellular, non-small cell lung, glioblastoma, osteosarcoma, pancreatic, and skin cancer cells, and/or inhibit liver and/or kidney fibrosis, and/or promote corneal epithelial wound healing.

(I)

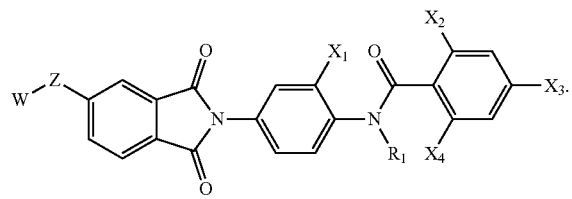

14 Claims, 14 Drawing Sheets

SIRTUIN 6 PROTEIN DEACYLASE (SIRT6) ACTIVATORS

PRIORITY

This application is a U.S. National Phase Application under 35 U.S.C. § 371 of International Application No. PCT/US2020/063353, filed Dec. 4, 2020 which claims priority to U.S. Provisional Patent Application No. 62/945,041, filed on Dec. 6, 2019, the entire contents of which are incorporated herein by reference in their entireties.

STATEMENT OF GOVERNMENT SUPPORT

This invention was made with government support under GM065386 awarded by the National Institutes of Health. The government has certain rights in the invention.

TECHNICAL FIELD

The present technology relates generally to classes of small molecule compounds that can activate sirtuin 6 protein deacylase (SIRT6). The present disclosure also includes pharmaceutical compositions and methods of use thereof. Specifically, the compounds and compositions of the present technology are useful in lowering LDL and/or triglyceride levels, increasing glucose tolerance, inhibiting proliferation of ovarian, colorectal, hepatocellular, non-small cell lung, glioblastoma, osteosarcoma, pancreatic, and skin cancer, and inhibiting nonalcoholic steatohepatitis and fibrotic kidney disease, and promote corneal wound healing.

BACKGROUND

The following description of the background of the present technology is provided simply as an aid in understanding the present technology and is not admitted to describe or constitute prior art to the present technology.

Sirtuins are an evolutionarily conserved family of proteins originally defined as the class III histone deacetylases (HDACs). While sirtuins can deacetylate histones, it is now widely accepted that these enzymes deacetylate diverse protein substrates and regulate many processes including metabolism and cellular stress response. This family of proteins share a conserved central catalytic domain and the ability to couple the cleavage of $NAD^+$ to the removal of an acyl group from the ε-amino group of lysines. Each family member (SIRT1-7) contains variable N-terminal and C-terminal domains and has diverse subcellular localization and function. Sirtuins bind substrate between a structural $Zn^{2+}$-binding domain and a Rossmann-fold domain in an isoform specific pocket, conferring distinct deacylase activities across family members.

SIRT6 has garnered the attention of scientists due to its vast repertoire of physiological roles. For example, SIRT6 overexpression lowers LDL and triglyceride levels, improves glucose tolerance, and increases the lifespan of male mice. Additionally, overexpression in ovarian, colorectal, hepatocellular, non-small cell lung, glioblastoma, osteosarcoma, pancreatic, and skin cancer cell lines inhibits proliferation. SIRT6 expression decreases with age. Loss of SIRT6 promotes fibrosis in several tissues and impairs corneal epithelial wound healing. SIRT6 therefore serves as a pharmacological target for small molecule activation.

SUMMARY

In an aspect, the present technology provides compounds of Formula I and pharmaceutically acceptable salts thereof,

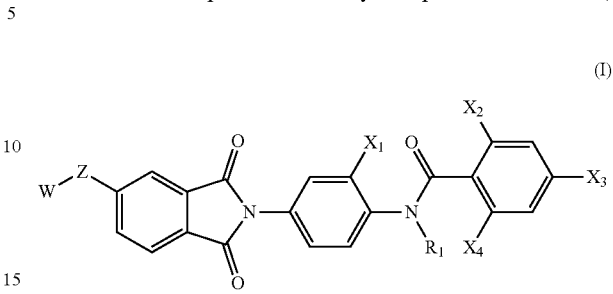

and pharmaceutically acceptable salts thereof, wherein

Z is absent or is $C(O)NH(CH_2)_nCH(R^4)$;

W is selected from a carboxyl, phosphoric acid, sulfuric acid, or ester group;

$X^1$ is H, F, Cl, or Br;

$X^2$, $X^3$, and $X^4$ is selected from H, F, Cl, or Br;

$R^1$ is H or C(O)-phenyl substituted with one or more of F, Cl, or Br;

$R^4$ is H or alkyl optionally substituted with a hydroxyl or phenyl group; and n is 0 or 1.

In an aspect, the present technology provides a pharmaceutical composition comprising a compound of Formula I, and a pharmaceutically acceptable carrier and/or a pharmaceutically acceptable excipient.

In an aspect, the present technology provides a method of activating SIRT6 comprising contacting SIRT6 with an effective amount of a compound of Formula I, a compound of Formula IV, $W^2$—$R^2$—Y—$R^3$, or a pharmaceutically acceptable salt thereof, wherein $W^2$ is selected from a carboxyl, phosphate or sulfate group; $R^2$ is a C1-C6 alkylene optionally substituted with a halo, hydroxyl or carboxyl group, a phenylene, a phenyl(C1-C6 alkylene), or a phenyl (C2-C6 alkenylene) group; Y is absent or is C(O), C(O)O, or C(O)NH; and $R^3$ is a C10 to C24 alkyl or alkenyl group, wherein the alkenyl group may have 1, 2, 3 or 4 double bonds.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1A:
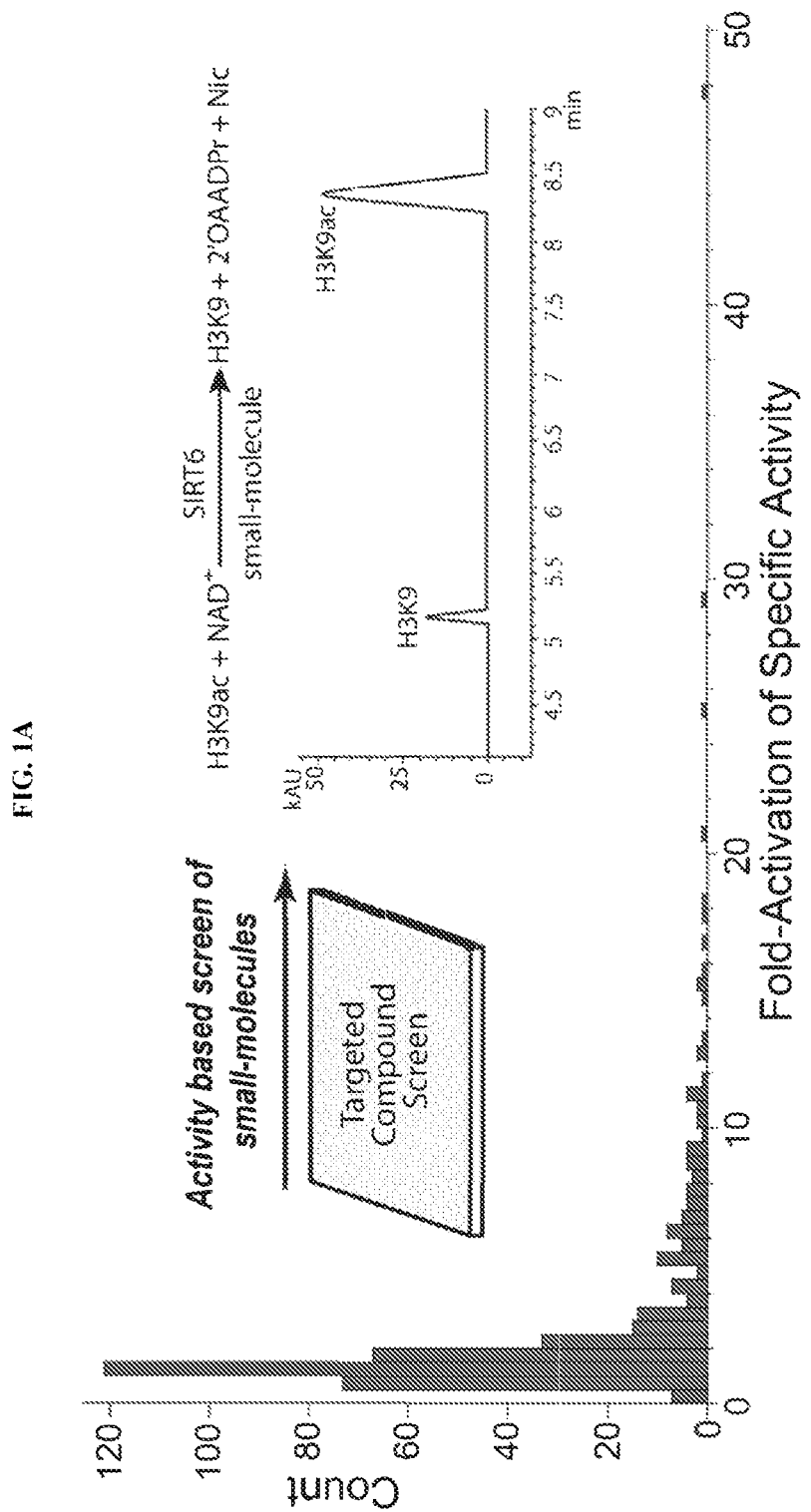
FIGS. 1A-F illustrate the identification of novel SIRT6 activators. (1A) Compound libraries BML-2803, BML-2800, and an additional set of 178 molecules were screened at 100 μM for their ability to stimulate SIRT6 (1 μM) deacetylation of H3K9ac peptide (20 μM) in the presence of 0.5 mM $NAD^+$. SIRT6 activity was measured by HPLC quantification of H3K9ac and deacetylated product (inset) and fold activations relative to DMSO control were determined and compiled. (1B) Fold-activation of SIRT6 (1 μM) determined in the presence of either 0-400 μM CL4, 0-150 μM TTNPB, 0-100 μM Lysophosphatidic acid (LPA), or 0-200 μM linoleoylglycine (LGly). Maximum fold-activation and $EC_{50}$ determined by sigmoidal curve fit. (1C) Steady-state kinetic analysis of SIRT6 (1 μM) deacetylation was conducted with 0-250 μM H3K9ac peptide in the presence of 100 μM CL4, 50 μM TTNPB, 50 μM LPA, or 50 μM LGly. Constants $K_{m,\ H3K9ac}$ and $k_{cat}$ were determined by fitting data to Michaelis-Menten equation. (1D) Fold-activations of SIRT1 (0.1 μM), SIRT2 (0.2 μM), SIRT3 (1 μM), SIRT5 (2 μM), and SIRT6 (1 μM) determined in the presence of CL4 (100 μM), TTNPB (50 μM), and LPA (50 μM) relative to DMSO control against 20 μM H3K9ac peptide and 0.5 mM NAD$^+$. Mean values reported with error bars representing standard deviation of at least three replicates. (1E) Fold activation of SIRT6 (1 μM) deacetylation of H3K9ac peptide (20 μM) in the presence of 0.5 mM NAD$^+$ and varying concentration of CL-5D (i.e., Formula III), SW-055, SW-062, and CL-126. (1F) Fold activation of SIRT6 (1 μM) deacetylation of H3K9ac peptide (20 μM) in the presence of 0.5 mM NAD$^+$ and varying concentration of CL-5D (i.e., Formula III), GX2-210, GX2-216, and GX2-217.

The definitions of certain terms as used in this specification are provided below. Unless defined otherwise, all technical and scientific terms used herein generally have the same meaning as commonly understood by one of ordinary skill in the art to which the present technology belongs.

The following terms are used throughout as defined below.

As used herein and in the appended claims, singular articles such as "a", "an", and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

Pharmaceutically acceptable salts of compounds described herein are within the scope of the present technology and include acid or base addition salts which retain the desired pharmacological activity and are not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

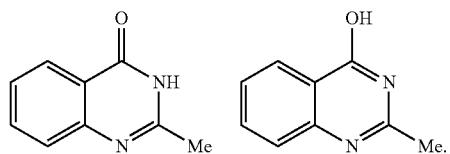

As another example, guanidines may exhibit the following isomeric forms in protic organic solution, also referred to as tautomers of each other:

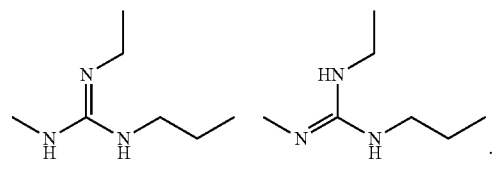

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or pharmaceutical compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include, but are not limited to, halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

As used herein, $C_m$-$C_n$, such as $C_1$-$C_{12}$, $C_1$-$C_6$, or $C_1$-$C_3$ when used before a group refers to that group containing m to n carbon atoms.

Alkyl groups include straight chain and branched chain alkyl groups having from 1 to 12 carbon atoms, and typically from 1 to 10 carbons or, in some embodiments, from 1 to 8, 1 to 6, or 1 to 3 carbon atoms. Examples of straight chain alkyl groups include, but are not limited to, groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Alkoxy groups are hydroxyl groups (—OH) in which the bond to the hydrogen atom is replaced by a bond to a carbon atom of a substituted or unsubstituted alkyl group as defined above. Examples of linear alkoxy groups include, but are not limited to, methoxy, ethoxy, propoxy, butoxy, pentoxy, hexoxy, and the like. Examples of branched alkoxy groups include, but are not limited to, isopropoxy, sec-butoxy, tert-butoxy, isopentoxy, isohexoxy, and the like. Examples of cycloalkoxy groups include, but are not limited to, cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Representative substituted alkenyl groups may be mono-substituted or substituted more than once, such as, but not limited to, mono-, di- or tri-substituted with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent alkenyl groups are alkenylene groups, divalent aryl groups are arylene groups (e.g., phenylene), and so forth. Substituted groups having a single point of attachment to the compound of the present technology are not referred to with the "ene" designation. Thus, e.g., chloroethyl is not referred to herein as chloroethylene.

The term "hydroxyl" as used herein can refer to —OH or its ionized form, —O—.

The present technology provides pharmaceutical compositions and medicaments comprising any of one of the embodiments of the compounds (drugs) disclosed herein and a pharmaceutically acceptable carrier or one or more excipients. The pharmaceutical compositions may be used in the methods and preventative treatments described herein. The pharmaceutical compositions may include an effective amount of any of one of the embodiments of the compounds of the present technology disclosed herein. In any of the above embodiments, the effective amount may be determined in relation to a mammalian subject. "Effective amount" refers to the amount of a compound or pharmaceutical composition required to produce a desired therapeutic and/or prophylactic effect. In the context of therapeutic or prophylactic applications, the amount of a compound or a composition administered to the subject will vary depending on the composition, the degree, type, and severity of the infection or risk of infection and on the characteristics of the individual. One example of an effective amount includes amounts or dosages that yield acceptable toxicity and bioavailability levels for therapeutic (pharmaceutical) use including, but not limited to, the reduction of LDL and/or triglyceride levels. As used herein, a "subject" or "patient" is a mammal, such as a cat, dog, rodent or primate. Typically the subject is a human, such as a human suffering from conditions sensitive to the compounds and pharmaceutical compositions of the present technology, e.g., levels of LDL and/or triglycerides capable of treatment with an effective amount of the compounds and compositions of the present technology. The term "subject" and "patient" can be used interchangeably.

As used herein, "administering" or the "administration" of a compound or pharmaceutical composition to a subject includes any route of introducing or delivering to a subject an effective amount of a compound or pharmaceutical composition of the present technology to perform its intended function. Administration can be carried out by any suitable route, including but not limited to, topical administration. Administration includes self-administration and the administration by another.

"Treating" or "treatment" within the context of the instant technology, means alleviation, in whole or in part, of symptoms, for example the symptoms of glucose intolerance, or abnormally high levels of LDL and/or triglycerides, associated with a disorder or disease, or slowing, inhibition or halting of further progression or worsening of those symptoms, or prevention or prophylaxis of the disease or disorder in a subject at risk for developing the disease or disorder. In the present context, "preventing" means the prevention in whole or in part of the condition, or disease being prevented, including at least one symptom associated therewith or caused thereby.

In an aspect, the present technology provides compounds of Formula I,

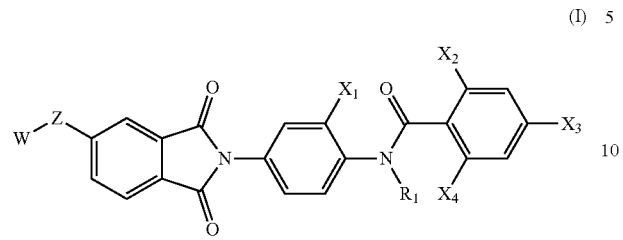

(I)

and pharmaceutically acceptable salts thereof, wherein

Z is absent or is $C(O)NH(CH_2)_nCH(R^4)$;

W is selected from a carboxyl, phosphoric acid, sulfuric acid, or ester group;

$X^1$ is H, F, Cl, or Br;

$X^2$, $X^3$, and $X^4$ is selected from H, F, Cl, or Br;

$R^1$ is H or C(O)-phenyl substituted with one or more of F, Cl, or Br;

$R^4$ is H or alkyl optionally substituted with a hydroxyl or phenyl group; and n is 0 or 1.

In any embodiments of the compounds of Formula I, Z may be absent. Alternatively, in any embodiments, Z may be $C(O)NH(CH_2)_nCH(R^4)$. In any embodiments, $R^4$ may be a $C_1$-$C_6$ alkyl (e.g., $C_1$-$C_4$ alkyl, $C_1$-$C_3$ alkyl, or $C_1$-$C_2$ alkyl) optionally substituted with a hydroxy or phenyl group. In any embodiments, $R^4$ may be $CH_2$-phenyl, $CH_2$—CH$(CH_3)_2$, or $CH_2$—OH. Alternatively, in any embodiments, $R^4$ may be H.

In any embodiments of the compounds of Formula I, W may be a carboxyl group. Reference to carboxyl will be understood to include its salt form, carboxylate, and vice versa. In any embodiments, W may be a phosphoric acid group; reference to phosphoric acid will be understood to include any of its phosphate salt forms. In any embodiments, W may be a sulfuric acid group; reference to sulfuric acid group will be understood to include any of its sulfate salt forms. In any embodiments, W may be an ester group. In any embodiments, W may be $C(O)$—O—$C_1$-$C_6$ alkyl including $C_1$-$C_4$ alkyl, $C_1$-$C_3$ alkyl, or $C_1$-$C_2$ alkyl. In any embodiments, W may be $C(O)$—$OCH_3$ or $C(O)$—$OCH_2CH_3$.

In any embodiments of the compounds of Formula I, at least one of $X^1$, $X^2$, $X^3$, and $X^4$ may not be H. In any embodiments, at least one of $X^2$, $X^3$, and $X^4$ may not be H. For example, at least one of $X^1$, $X^3$, and $X^4$ may be Cl and/or at least one of $X^2$, $X^3$, and $X^4$ may be Cl. In any embodiments, $X^2$ may be Cl, or $X^3$ may be Cl, or $X^4$ may be Cl. In any embodiments, $X^2$ and $X^3$ may be Cl, or $X^3$ and $X^4$ may be Cl, or $X^2$ and $X^4$ may be Cl. In any embodiments, each of $X^2$, $X^3$, and $X^4$ may be Cl. In any embodiments, each of $X^1$, $X^2$, $X^3$, and $X^4$ may be Cl.

In any embodiments of the compounds of Formula I, $R^1$ may be H. In any embodiments, $R^1$ may be C(O)-phenyl substituted with one or more of F, Cl, or Br. For example $R^1$ may be C(O)-phenyl may be substituted with 1, 2 or 3 Cl, or 1, 2, or 3 F, or 1, 2, or 3 Br, or a mixture of any of the preceding substituents. In any embodiments, $R^1$ may have the structure of Formula II,

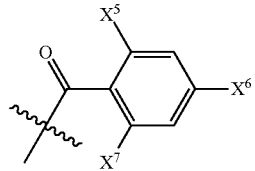

(II)

wherein $X^5$, $X^6$, and $X^7$ are independently selected from H, F, Cl, or Br, provided that at least one of $X^5$, $X^6$, and $X^7$ is not H. For example, $X^5$ may be Cl, or $X^6$ may be Cl, or $X^7$ may be Cl. In any embodiments, $X^5$ and $X^6$ may both be Cl (or F or Br), or $X^5$ and $X^7$ may both be Cl (or F or Br), or $X^6$ and $X^7$ may both be Cl (or F or Br). In any such embodiments, each of $X^5$, $X^6$, and $X^7$ is Cl.

In any embodiments, the compound of Formula I and pharmaceutically acceptable salts thereof may be a compound selected from

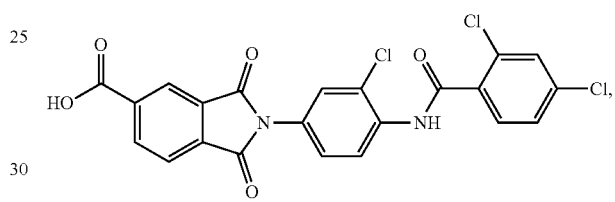

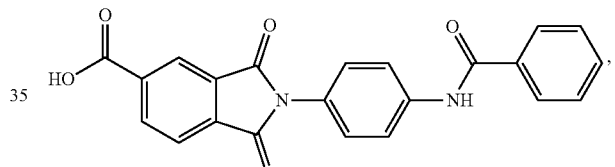

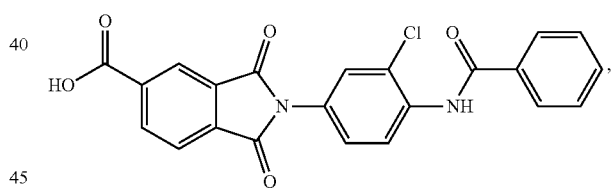

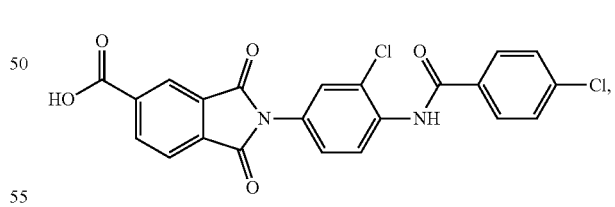

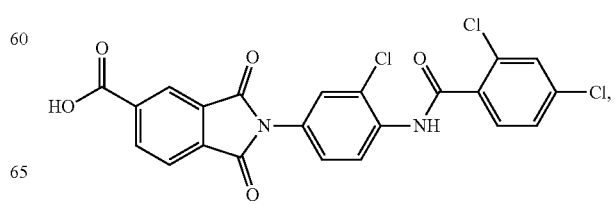

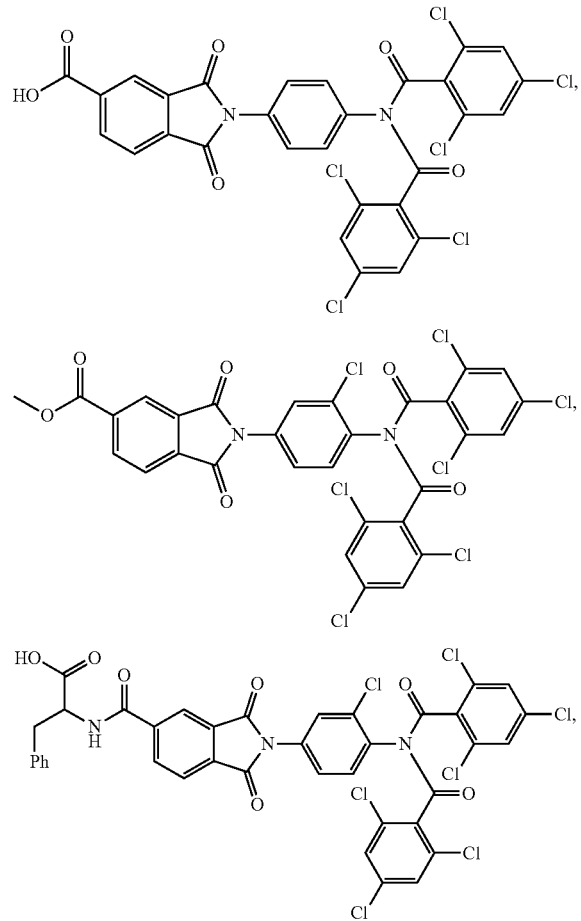

In any embodiments, the compound of Formula I and pharmaceutically acceptable salts thereof may be a compound of Formula III and pharmaceutically acceptable salts thereof,

III

Herein, Formula III may also be referred to as CL-5D.

In an aspect, the present technology provides a method of activating SIRT6 comprising contacting SIRT6 with an effective amount of any compound of Formula I described herein, a compound of Formula IV, $W^2$—$R^2$—Y—$R^3$, or a pharmaceutically acceptable salt thereof, wherein $W^2$ is selected from a carboxyl, phosphate or sulfate group; $R^2$ is a C1-C6 alkylene optionally substituted with a halo, hydroxyl or carboxyl group, a phenylene, a phenyl(C1-C6 alkylene), or a phenyl(C2-C6 alkenylene) group; Y is absent or is C(O), C(O)O, or C(O)NH; and $R^3$ is a C10 to C24 alkyl or alkenyl group, wherein the alkenyl group may have 1, 2, 3 or 4 double bonds. In any embodiments, the method includes contacting SIRT6 with an effective amount of a compound of Formula I or III. In any embodiments, the method is an in vitro method, e.g., using isolated wild-type or recombinant SIRT6, or cell culture of cells comprising SIRT6. In any embodiments, the method is an in vivo method, e.g., the compound is administered to a subject (e.g., human, dog, cat, primate).

In an aspect, the present technology provides methods of treatment comprising administering an effective amount of any compound described herein (including but not limited to any compound of Formula I, III, or IV described herein) to a subject in need thereof to lower LDL levels, lower triglyceride levels, and/or increase glucose tolerance in the subject.

In an aspect, the present technology provides methods of inhibiting proliferation of ovarian, colorectal, hepatocellular, non-small cell lung, glioblastoma, osteosarcoma, pancreatic, and skin cancer cells comprising contacting said cells with an effective amount of any compound described herein (including but not limited to any compound of Formula I, III, or IV described herein).

In an aspect, the present technology provides methods of treatment comprising administering an effective amount of any compound described herein (including but not limited to any compound of Formula I, III, or IV described herein) to a subject in need thereof to inhibit liver and/or kidney fibrosis in the subject.

In an aspect, the present technology provides methods of treatment comprising administering an effective amount of any compound described herein (including but not limited to any compound of Formula I, III, or IV described herein) to a subject in need thereof to promote corneal epithelial wound healing.

In any embodiment disclosed herein, the subject is a mammal, e.g., a human, a monkey, a chimpanzee, an ape, a cat, a dog, a pig, a mouse, a rat, a horse, or a sheep. Additionally or alternatively, in some embodiments of the methods, the subject is a human.

Those skilled in the art are readily able to determine an effective amount for the present methods by simply administering a compound of the present technology to a subject in increasing amounts until, for example, LDL and/or triglyceride levels are reduced (e.g., as measured using standard laboratory assays), glucose tolerance is increased, ovarian, colorectal, hepatocellular, non-small cell lung, glioblastoma, osteosarcoma, pancreatic, and skin cancer cell proliferation inhibited, liver and/or kidney fibrosis is inhibited, or corneal epithelial wound healing is increased. The compounds of the present technology can be administered to a patient at dosage levels in the range of about 0.1 to about 1,000 mg per day or higher. For a normal human adult having a body weight of about 70 kg, a dosage in the range of about 0.01 to about 100 mg per kg of body weight per day is sufficient, or even about 0.1 to 50 mg/kg of body weight per day. The specific dosage used, however, can vary or may be adjusted as considered appropriate by those of ordinary skill in the art. For example, the dosage can depend on a number of factors including the requirements of the patient, the condition being treated, and the pharmacological activity of the compound being used. The determination of optimum dosages for a particular patient is well known to those skilled in the art.

The instant present technology provides pharmaceutical compositions and medicaments comprising any of the compounds disclosed herein (e.g., compounds of Formula I, III, IV) and a pharmaceutically acceptable carrier or one or more excipients or fillers. The compositions may be used in the methods and treatments described herein. Such compositions and medicaments may include a therapeutically effective amount of any compound as described herein, including but not limited to a compound of Formula I (including but not limited to III) or IV, pharmaceutically acceptable salts thereof, stereoisomers thereof, tautomers thereof and/or solvates thereof. The pharmaceutical composition may be packaged in unit dosage form. The unit dosage form is effective for activating SIRT6, lowering LDL and/or triglyceride levels, increasing glucose tolerance, inhibiting proliferation of ovarian, colorectal, hepatocellular, non-small cell lung, glioblastoma, osteosarcoma, pancreatic, and skin cancer cells, inhibiting liver and/or kidney fibrosis, and/or promoting corneal epithelial wound healing.

The pharmaceutical compositions and medicaments may be prepared by mixing one or more compounds of the present technology, pharmaceutically acceptable salts thereof, stereoisomers thereof, tautomers thereof, or solvates thereof, with pharmaceutically acceptable carriers, excipients, binders, diluents or the like. The compounds and compositions described herein may be used to prepare formulations and medicaments that activate SIRT6 and/or treat conditions mediated or influenced by SIRT6 activation. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Additionally or alternatively, in some embodiments, the pharmaceutical composition may comprise a pharmaceutically acceptable excipient. Exemplary pharmaceutically acceptable excipients include, but are not limited to, cetyl esters, wax, cetyl alcohol, white wax, glyceryl monostearate, propylene glycol monostearate, methyl stearate, benzyl alcohol, sodium lauryl sulfate, glycerin, mineral oil, water, carbomer, ethyl alcohol, acrylate adhesives, polyisobutylene adhesives, silicone adhesives, as well as a combination of any two or more thereof.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the dosage forms described herein and containing effective amounts are well within the bounds of routine experimentation and therefore, well within the scope of the instant present technology.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

EXAMPLES

The present technology is further illustrated by the following examples, which should not be construed as limiting in any way.

Experimental Procedures

Expression and Purification of Recombinant SIRT1, SIRT2, SIRT3, SIRT5, and SIRT6

His-tagged SIRT1, SIRT2, SIRT3, SIRT5, and SIRT6 were expressed in BL21 DE3 *E. coli* following induction by 0.5 mM IPTG at $OD_{600}$ of 1-1.2 at 25° C. and 12 hours of subsequent growth prior to harvest. Cells were resuspended in 50 mM sodium phosphate, pH 7.2, 250 mM NaCl, 5 mM imidazole, 1 mM β-mercaptoethanol, and protease inhibitors (aprotinin 2 μg/mL, leupeptin 2 μg/mL, pepstatin 1 μg/mL, and AEBSF 0.5 mM). Cell suspension was lysed by 3 passes through EmulsiFlex-05 (Avestin) at 10,000-15,000 psi, clarified at 50,000×g at 4° C., and purified by nickel affinity chromatography. SIRT6 used in ITC and quench-flow was further purified using heparin ion-exchange chromatography. Following nickel chromatography and overnight dialysis in to 50 mM sodium phosphate, pH 7.2, 50 mM NaCl, 5% glycerol, and 1 mM β-mercaptoethanol, SIRT6 was loaded on pre-equilibrated HiTrap Heparin HP affinity column (GE). SIRT6 was eluted on a linear gradient from 50 to 1000 mM NaCl in 50 mM sodium phosphate, pH 7.2, and 1 mM β-mercaptoethanol. Fractions containing SIRT6 were pooled, concentrated, and dialyzed into 50 mM Tris, pH 8.0

(4° C.), 150 mM NaCl, 100 μM TCEP, and 5% (w/v) glycerol. Protein concentrations were determined by Bradford.

Synthesis and Analysis of H3K9 Peptides

Peptides corresponding to residues 4-17 of histone H3 (Acetyl: Ac-KQTARKacSTGGKAPR-WW—NH$_2$, and Myristoyl: Ac-KQTARKmyrSTGGKAPRWW-NH$_2$) were synthesized by standard Fmoc-solid phase peptide synthesis. Two tryptophan residues were added to the C-terminus for quantification at 280 nm. Nε-Acetyl-L-lysine was directly incorporated to position 9 of the acetyl peptide however for the myristoylated peptide the side chain of lysine 9 was protected with 1-(4,4-dimethyl-2,6-dioxocyclohex-1-ylidene)-3-methylbutyl (ivDde) group. Following synthesis of both peptides, the amino terminus was acetylated using acetic anhydride. The ivDde group was then removed by incubating the peptide-resin with 4% hydrazine in dimethylformamide (DMF) for 10 minutes. The liquid was extracted and the incubation was repeated for a total of seven times. The peptide-resin was then incubated with 528 mM myristic anhydride in toluene overnight. The resin was then washed with DMF followed by dichloromethane (DCM). The peptides were cleaved with a mixture of trifluoroacetic acid (TFA), 5% thioanisole, and 2.5% ethanedithiol. The cleaved crude peptides were then precipitated in ice-cold ether and re-suspended in water and lyophilized. The peptides were purified over a preparative C18 HPLC column. The chromatographic purity of the peptide was determined to be >95% and mass spectrometric analysis on a Bruker REFLEX II: MALDI-TOF (matrix-assisted laser desorption ionization time-of-flight) instrument confirmed the identity of the peptide. The peptides were then dissolved in water.

Small Molecule SIRT6 Activator Screen

In collaboration with University of Wisconsin's Small Molecule Screening Facility (UWSMSF), compounds from BML-2803 and BML-2800 (Enzo Life Sciences), and 178 cherry-picked compounds from UWSMSF libraries were distributed to 384-well plates using Biomek 2000 (Beckman). Mastermix containing SIRT6, buffer, and H3K9ac peptide were distributed to wells using Microflex peristaltic dispenser (Beckman). Plates were spun and preheated to 37° C. before addition of NAD$^+$ using peristaltic dispenser. After 60 minutes reactions were quenched with 2% TFA final using peristaltic dispenser then sealed and spun again before in-house HPLC separation and quantification of substrate and product peptides. Reaction conditions were 1 μM SIRT6, 0.5 mM NAD$^+$, 20 mM H3K9ac (4-16), 20 mM potassium phosphate pH 7.5, 10% DMSO, and either 10 or 100 μM compound determined by 10-fold dilution of stock library concentration.

Steady-State Sirtuin Deacylation Assay and HPLC Analysis

All sirtuin deacylation assays were carried out at 37° C. in 20 mM potassium phosphate pH 7.5 with 0.5 mM NAD$^+$, 10% DMSO, and 20 μM H3K9ac or H3K9myr peptides, unless otherwise noted in legend, and quenched by the addition of 2% TFA final. Steady-state reactions were constrained to less than 20% substrate turnover to prevent product inhibition. A variety of times were required to monitor SIRT6 deacetylation (2-60 minutes) under this restraint given the ability to strongly activate catalysis. In these cases, specific activities were determined and either reported as is or as fold-activation of specific activity. Deacylation reactions were analyzed by reversed phase high-performance liquid chromatography on a Kinetex C18 column (100 Å, 100×4.6 mm, 2.6 μm, Phenomenex) by monitoring the formation of the deacylated product at 214 nm. Deacetylation reactions were analyzed using a gradient of 33-100% B (30% acetonitrile with 0.05% TFA) in 8 min at 1.6 mL min$^{-1}$. Demyristoylation reactions were analyzed using a gradient of 3 to 100% B (acetonitrile with 0.05% TFA) in 10 min at 1.6 mL min$^{-1}$. The product and substrate peaks were quantified and ratio of these allowed for quantification of product formation. Three independent experiments were performed for each condition with averages being plotted and error bars representing the standard deviation of these replicates.

Synthesis of CL5D and Derivatives

Step1. A mixture of 2-chloro-4-nitroaniline (400 mg, 2.32 mmol) and 2,4,6-trichloro benzoyl chloride (682 mg, 2.8 mmol) was made to which DIEA (0.85 mL, 5.1 mmol) and dichloroethane (0.5 mL) were added. The 2,4,6-trichloro benzoyl was substituted with either benzoyl chloride to produce CL-5 and CL-5A, or 4-chloro benzoyl chloride to produce CL-5B. The synthesis of CL-5 further required 2-chloro-4 nitroaniline to be substituted for 4-nitroaniline. The resulting solution was stirred at 100° C. overnight. The reaction was cooled down to room temperature, diluted by methylene chloride, and quenched by sodium bicarbonate. The organic layer was separated, washed with brine, and dried over sodium sulfate. The solvent was evaporated and the resulting residue was purified via flash chromatography (hexane/ethyl acetate 5:1) which yielded a solid (568 mg, 69% yield).

Step2: The resultant amide (568 mg, 0.97 mmol) and iron (840 mg, 15 mmol) were added into a solution of 10% aqueous HCl (12 mL), methanol (13 mL), and water (13 ml). The mixture was stirred at 60° C. for 3 hours. After the starting material disappeared, the solution was quenched by saturated sodium carbonate and extracted with ethyl acetate. The combined organic layers were dried over sodium sulfate. The solvent was evaporated and the resulting residue was purified by flash chromatography (hexane/ethyl acetate 4:1) which yielded a solid (402 mg, 74% yield).

Step3: The resultant aniline (102 mg, 0.18 mmol) and trimellitic anhydride (65.3 mg, 0.34 mmol) were added acetic acid (10 mL). The resulting solution was stirred at 130° C. overnight. The reaction was then cooled to room temperature. The solid precipitate was filtered and washed with water and ethanol to yield the final product (CL5D yielded 70 mg, 53% yield). Each product was verified by $^1$H-NMR, $^{13}$C-NMR, and LC-MS. See Table 3 below for structures.

CL-5A: 47% yield. $^1$H NMR (400 MHz, (CD$_3$)$_2$SO) δ 10.18 (s, 1H), 8.39-8.40 (d, J=4 Hz, 1H), 8.29 (s, 1H), 8.05-8.07 (d, J=8 Hz, 1H), 7.97-7.99 (d, J=8 Hz, 2H), 7.68-7.73 (m, 2H), 7.58-7.60 (m, 1H), 7.46-7.54 (m, 3H). $^{13}$C NMR (400 MHz, (CD$_3$)$_2$SO) δ 166.81, 166.54, 166.26, 136.25, 135.68, 135.42, 134.46, 132.71, 130.96, 130.09, 129.27, 129.20, 128.96, 128.47, 127.22, 127.20, 124.58, 124.17. ESI MS [M-H]−, calc. 419.0440, obs. 419.0446.

CL-5B: 55% yield. $^1$H NMR (400 MHz, (CD$_3$)$_2$SO) δ 10.32 (s, 1H), 8.43-8.45 (q, J=1.2 Hz, 1H), 8.34 (s, 1H), 8.11-8.12 (s, J=4 Hz, 1H), 8.03-8.05 (d, J=8 Hz, 2H), 7.73-7.76 (m, 2H), 7.64-7.66 (d, J=8 Hz, 2H), 7.51-7.53 (m, 1H). $^{13}$C NMR (400 MHz, (CD$_3$)$_2$SO) δ 166.76, 166.74, 166.51, 165.27, 137.56, 137.34, 136.27, 135.58, 135.48, 133.22, 132.76, 131.11, 130.44, 130.17, 129.37, 129.31, 128.97, 127.23, 124.64, 124.17. ESI MS [M-H]−, calc. 453.0051, obs. 453.0057.

CL5D: $^1$H NMR (400 MHz, DMSO-d6) δ 8.43 (d, J=7.7 Hz, 1H), 8.31 (s, 1H), 8.09 (d, J=7.8 Hz, 1H), 7.96-7.70 (m, 6H), 7.53 (d, J=8.5 Hz, 1H). $^{13}$C NMR (101 MHz, DMSO) δ 165.72, 165.56, 164.15, 163.97, 136.64, 136.18, 135.65, 134.68, 134.26, 133.41, 131.87, 131.37, 130.07, 128.60, 128.38, 128.27, 128.02, 126.41, 124.01, 123.52. LCMS (Purity: 93.12%, Calc. [M-H]−: 726.8364; Obs. 726.8377).

The amide derivatives of CL5D were synthesized generally following Scheme 1. CL5D (1 eq), amine (1.5 eq) and TEA (2 eq) were dissolved in dry DMF (0.1 M) followed by addition of HATU (1.5 eq). After stirring overnight, the reaction mixture was diluted with EtOAc, and washed with water and brine. The mixture was concentrated under vacuum and purified using silica gel chromatography to provided the ester intermediate. The ester intermediate was dissolved in TFA and DCM (v/v=1:1, 0.1 M). After stirring for 4 hours, the reaction mixture was concentrated in vacuo. The residue was purified by silica gel chromatography to provide the product.

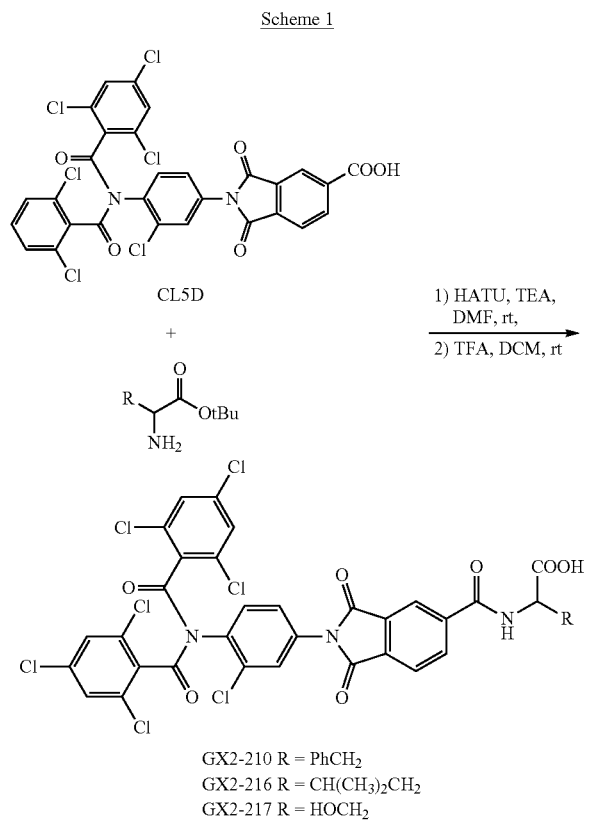

Scheme 1

GX2-210 R = PhCH$_2$
GX2-216 R = CH(CH$_3$)$_2$CH$_2$
GX2-217 R = HOCH$_2$

Each product was verified by $^1$H-NMR, $^{13}$C-NMR, and LC-MS.

GX2-210: $^1$H NMR (500 MHz, CDCl$_3$) δ 8.20 (s, 1H), 8.14 (d, J=7.5 Hz, 1H), 7.94 (d, J=7.7 Hz, 1H), 7.71 (dd, J=14.5, 5.3 Hz, 2H), 7.51-7.35 (m, 2H), 7.33-7.13 (m, 5H), 6.98 (d, J=5.8 Hz, 1H), 5.08 (d, J=3.9 Hz, 1H), 3.36 (dd, J=13.5, 4.4 Hz, 1H), 3.21 (dd, J=13.7, 6.2 Hz, 1H). $^{13}$C NMR (126 MHz, CDCl$_3$) δ 165.85, 165.46, 164.47, 140.02, 135.55, 135.39, 134.39, 133.98, 133.78, 132.61, 131.77, 130.33, 129.44, 129.05, 127.74, 124.63, 124.36, 122.69, 77.48, 77.23, 76.98, 37.45. HRMS (M-H): 873.9050.

GX2-216: $^1$H NMR (500 MHz, CDCl$_3$) δ 8.29 (s, 1H), 8.24 (d, J=7.7 Hz, 1H), 7.93 (d, J=7.7 Hz, 1H), 7.71 (dd, J=11.5, 5.1 Hz, 2H), 7.46-7.36 (m, 2H), 7.26 (s, 1H), 7.19 (d, J=21.4 Hz, 2H), 4.83 (d, J=4.4 Hz, 1H), 1.89-1.70 (m, 3H), 0.98 (d, J=2.9 Hz, 6H). $^{13}$C NMR (126 MHz, CDCl$_3$) δ 176.62, 165.98, 165.46, 164.47, 140.01, 135.35, 134.63, 133.94, 133.70, 132.60, 131.66, 130.34, 127.75, 124.57, 124.39, 122.71, 77.48, 77.23, 76.98, 51.87, 41.11, 25.27, 23.04, 21.92. HRMS (M-H): 839.9207.

GX2-217: $^1$H NMR (500 MHz, CDCl$_3$) δ 8.22 (s, 1H), 8.13 (s, 1H), 7.98 (s, 1H), 7.76 (s, 1H), 7.70-7.61 (m, 1H), 7.38 (d, J=21.3 Hz, 2H), 7.15 (d, J=21.5 Hz, 1H), 4.70 (s, 1H), 4.10 (dd, J=21.6, 14.3 Hz, 1H), 3.90 (s, 1H). HRMS (M-H): 813.8688.

Histone Extraction and Immunoblot

HEK293T cells were cultured in Dulbecco's Modified Eagle Medium supplemented with 10% fetal bovine serum. Cells were treated with 10 μM SAHA for 24 hours prior to harvest. Cells were trypsinized and pelleted prior to washing twice with ice-cold PBS. Cells were then resuspended in 800 μL ice-cold 10 mM HEPES pH 7.4, 10 mM KCl, 0.05% NP-40, and histone deacetylase and protease inhibitors (1 mM sodium butyrate, 4 μM trichostatin A, 100 μM phenylmethylsulfonyl fluoride, 10 μg/mL leupeptin, and 10 μg/mL aprotinin) for 20 minutes. After a 1,000×g 10 minute spin at 4° C. the pelleted nuclei were resuspended in 0.2 M HCl and incubated on ice for 20 minutes. Following 10 minute spin at 21,000×g at 4° C. the acid extracted supernatant was neutralized with 1 M Tris-HCl pH 8 prior to BCA protein concentration measurement. Histone deacetylation assays were ran with 75 μg/mL extracted histones, 1 μM SIRT6, 50 μM CL5, CL5D or 5% DMSO control, 0.5 mM NAD$^+$, in 20 mM potassium phosphate pH 7.5. Reactions ran at 37° C. prior to quench with SDS loading dye and 5 minute boil. 540 ng of nuclei acid extract following sirtuin reaction were loaded for 15% SDS-PAGE followed by transfer to nitrocellulose. Membrane was blocked with 1% milk before blotted with anti-H3K9ac (Active Motiff 39917) 1:3000 and imaged. Membrane then stripped with Thermo Restore PLUS Strip for 10 minutes then blocked and blotted with anti-H3 (Abcam 46765) 1:3000 and reimaged. Prior to imaging, 800 CW anti-rabbit IgG (LiCor 925-32211) 1:10,000 was incubated on membrane and imaging was conducted on Adyssey (LiCor). Bands were quantified using Image Studio Lite (LiCor).

Partial Proteolysis

SIRT6 wt or R65A (0.67 mg/mL) was mixed with either no ligand, NAD$^+$ (300 μM), ADPr (300 μM), or CL5D (50 μM) in 20 mM potassium phosphate pH 7.5 and DMSO 0.5%. Subtilisin was added to this mixture at a final concentration of 67 ng/mL with a final reaction volume of 15 μL. Reactions were incubated for 15 minutes at 22° C. and quenched by the addition of 5 μL 5×SDS-PAGE loading buffer followed by immediate 5 minute incubation at 95° C. Quenched reactions (3-5 μg SIRT6) were subjected to electrophoresis on a 15% acrylamide gel prior to Coomassie staining.

Fluorescence Polarization

Reactions (20 μL) were assembled in black flat bottom non-binding 384 well plates containing SIRT6 WT or R65A (0-80 μM), 1.25% glycerol w/v, 12.5 mM Tris pH 8, 20 mM potassium phosphate pH 7.5, 37.5 mM NaCl, 25 μM TCEP, and 20 nM FAM-labeled peptide. SIRT6 was diluted to 4× final concentration in final dialysis buffer prior to addition to 384 well plate to normalize for dialysis buffer contribution. Peptide was either FAM-H3K9ac (FAM-PEG4-KQTARKacSTGGKAPR-NH$_2$) or FAM-H3K9myr (FAM-PEG4-KQTARKmyrSTGGKAPR-NH$_2$). Reaction plate was spun at 300×g for 2 minutes and incubated at room temperature for 10 minutes prior to read. Three independent experiments were performed for each condition with averages being plotted and error bars representing the standard deviation of these replicates.

Global Bisubstrate Kinetic Analysis

Bi-substrate kinetic analysis of SIRT6 (0.25 µM) demyristoylation was performed at concentrations of NAD⁺ spanning 1-500 µM and H3K9myr spanning 0.33-27 µM all in 20 mM potassium phosphate pH 7.5 and 10% DMSO. SIRT6 was preincubated to 37° C. with varying concentrations of H3K9myr prior to catalytic initiation by addition of varying concentrations of NAD⁺. Reactions were carried out in 20 µL final in a 384-well plate and quenched after 3 minutes by the addition of 20 uL 4% TFA in acetonitrile. Demyristoylated peptide product was quantified by HPLC as described in steady-state sirtuin deacylation assay methods section. Rates of demyrisotylation were determined and data were globally fitted to a sequential ordered Bi—Bi equation (see below) using KinetAsyst (IntelliKinetics, State College, PA) and a nonlinear least squares analysis in order to determine $V_{max}$, $K_{m,H3K9myr}$, $K_{m,NAD+}$, $K_{d,H3K9myr}$, $K_{d,NAD+}$, $V/K_{m,H3K9myr}$, and $V/K_{m,NAD+}$.

$$v = \frac{V_{max} * [NAD^+] * [H3K9myr]}{K_{d,NAD} * K_{m,H3K9myr} + K_{m,NAD} * [H3K9myr] + K_{m,H3K9myr} * [NAD^+] + [NAD^+] * [H3K9myr]}$$

Thermal Denaturation Assay

Differential scanning fluorimetry was used to determine the melting temperature ($T_m$) of WT and R65A SIRT6. Proteins were diluted to 10 µM (20 mM sodium phosphate, pH 7.5) containing 3.75× Sypro Orange (Invitrogen, delivered at 5000×). Samples (35 µL) were aliquoted into PCR strip tubes and placed in a Bio-Rad CFX96 RealTime System C1000 thermal cycler. The temperature was increased at a rate of 0.5° C./min over a range of 10-95° C. and fluorescence was monitored with the FRET channel. Three trials were performed for each SIRT6 variant. The measured fluorescence was normalized so that the minimum fluorescence was set to 0 and the maximum fluorescence set to 1. The data were fit as previously reported (39) to obtain the $T_m$. Three independent experiments were performed for each SIRT6 variant with the mean being plotted and error bars representing the standard deviation of these replicates.

Isothermal Titration Calorimetry

ITC was conducted using a VP-ITC microcalorimeter from MicroCal, LLC (Northampton, MA). Titrations were performed in 50 mM Tris, pH 7.5 (25° C.), 150 mM NaCl, 100 µM TCEP, 0.5% DMSO and 5% (w/v) glycerol. Ligands (ADPr and synthesized H3K9ac) were suspended in the dialysis buffer used to store SIRT6. H3K9ac peptide (0.6 mM) and ADPr (0.5 mM) was titrated in to SIRT6 (27 µM) and ADPr (0.5 mM). The same titration was conducted in which both the syringe and cell contained 50 µM CL5D. For each experiment, 37 injections (1-8 µl) were titrated into the cell (initial cell volume 1.42 ml) while being stirred at 300 rpm. Each titration was also performed in the absence of SIRT6 and the background heats of titration were subtracted from the corresponding experimental measurements prior to fitting. Experimental data were fit to a one-site binding model using Origin scientific plotting software as previously described (31). Each titration was performed in triplicate with mean $K_d$ value reported with error bars representing standard deviation of the measurements. A single representative curve is shown for each titration.

Rapid Quench Flow Kinetics

Single-turnover kinetics to determine the rates of nicotinamide and demyristoylated peptide formation were performed using a Hi-Tech RQF-63 device (Hi-Tech Scientific, Bradford-on-Avon, U.K.) as previously described (40). Reactions contained SIRT6 WT or R65A (18 µM), 300 µM NAD⁺, 5 µM H3K9myr, and 20 mM potassium phosphate pH 7.5. Reactions were monitored from 1-100 seconds and automatically quenched with TFA to a final concentration of 1%. Nicotinamide and demyristoylated peptide were separated by reverse-phase HPLC using a gradient of 0-4% B (100% ACN with 0.05% TFA) over 12.5 minutes followed by 20-100% B over 30 minutes on a Vydac 201SP104 C18 column. Buffer A was water with 0.05% ACN. Nicotinamide peaks were integrated at 260 nm and quantified based on a standard curve of nicotinamide. Demyristoylated peptide product was determined as described above for steady-state kinetics. The first-order rate constants (k) of product formation were determined by fitting quantified product to a single-exponential equation, $P=[S]_0(1-e^{-kt})$, where P is the concentration of product formed, $[S]_0$ is the initial concentration of H3K9myr, and t is the reaction time (41). Each progression curve was performed in triplicate with mean product formed at each time point plotted with error bars representing the standard deviation of the measurements.

Burst Kinetic Analysis of SIRT6 Deacetylation.

SIRT6 (10 µM) was mixed with either H3K9ac peptide (400 µM) or NAD⁺ (500 µM) in 20 mM potassium phosphate pH 7.5 and preheated to 37° C. for 3 minutes. Reactions were initiated either through the addition of NAD⁺ (500 µM final) or H3K9ac peptide (400 µM final) and quenched after 10-1800 seconds by the addition of 3% TFA final. For each experiment, a control reaction in which H3K9ac peptide was excluded was collected at each timepoint and subtracted from corresponding experimental reactions to control for NAD⁺ degradation. Nicotinamide and deacetylated peptide product were quantified by reverse-phase HPLC as described in the rapid quench flow kinetics methods section.

Example 1: Targeted Screen for SIRT6 Activators

A targeted screen of diverse fatty acid (FA) and lipid-like molecules (FIG. 1A) was conducted to identify SIRT6 allosteric activators.

Two compound libraries were selected for initial targeted screening comprising 64 fatty acids (BML-2803) and 190 bioactive lipids (BML-2800). Each compound was screened at 100 µM for its ability to stimulate SIRT6 deacetylation against a histone H3 acetyl-lysine 9 (H3K9ac) peptide. H3K9ac substrate and H3K9 product were separated and quantified by HPLC to determine rates of reaction. Structural analysis of the positive hits identified from the two compound libraries revealed two distinct substructure clusters beyond that of previously reported FFAs: Conjugated fatty acids (7) and aromatic carboxylates (6). Based on this analysis, an additional 178 compounds related to the aforementioned compound classes were selected from the University of Wisconsin Small Molecule Screening Facility's libraries for subsequent screening.

In total 432 compounds were screened with 71 (16%) displaying over 5-fold activation and 23 (5%) displaying over 10-fold activation. Table 1 shows the structures of the top 10 identified SIRT6 activators with corresponding fold-activations (F.A.) at 100 µM. Of the 71 compounds displaying greater than 5-fold activation in SIRT6 specific activity, 97% contain a terminal negative charge carried by a carboxylic acid, phosphate, or sulfate, and 89% contain a linear aliphatic chain. As expected, a number of FFAs were capable of activating SIRT6, accounting for 70% of the identified hits displaying between 5 and 12-fold activation. A positive control, myristic acid, displayed a 3.7-fold activation, consistent with previous reports under the same conditions (21). Ten compounds displayed greater than 15-fold activation from which oleoyl-lysophosphatidic acid (LPA), linoleoyl-glycine (L-Gly), arotinoid acid (TTNPB), and 2-(3-chloro-4-(2,4-dichlorobenzamido)phenyl)-1,3-dioxoisoindoline-5-carboxylic acid (CL-4) were selected for further characterization (Table 1).

TABLE 1

| Compound ID | Structure | F.A. |
|---|---|---|
| Lysophosphatidic acid | 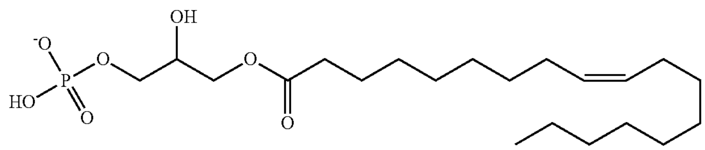 | 48 |
| N-Linoleoylglycine | 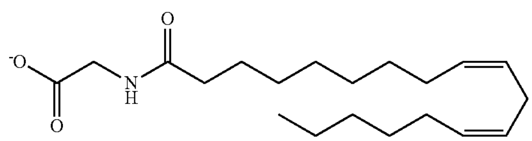 | 29 |
| 2-Fluoropalmitic acid | 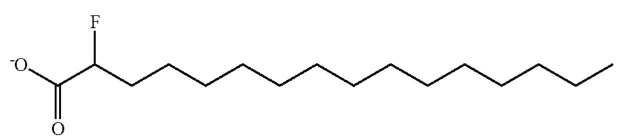 | 25 |
| TTNPB | 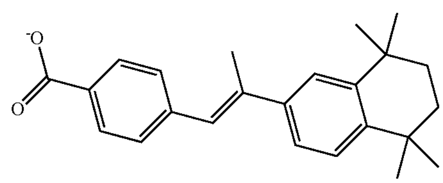 | 21 |
| CL-4 | 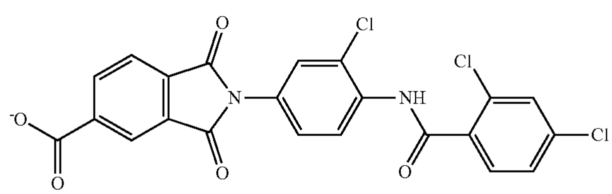 | 18 |
| L-NASPA | 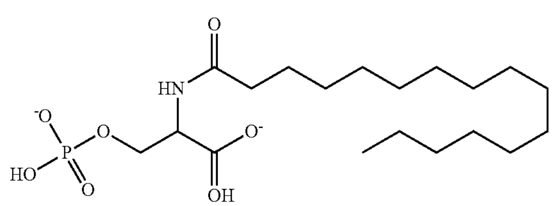 | 18 |
| Eicosatrienoic acid (20:3 n-3) | 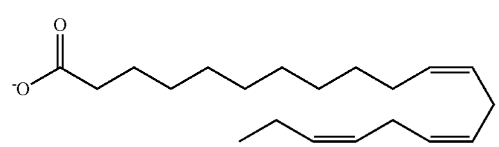 | 17 |
| Mead acid (20:3 n-9) | 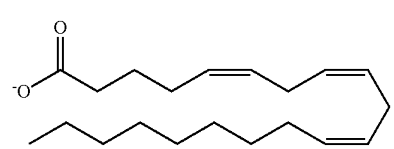 | 16 |
| Arachidonic acid (20:4 n-6) | 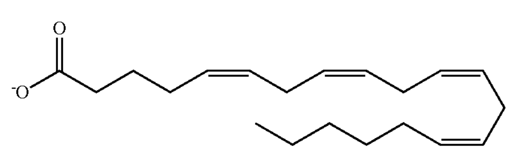 | 15 |

Example 2: Biochemical Characterization of Small Molecule Activators

Figure 1B:
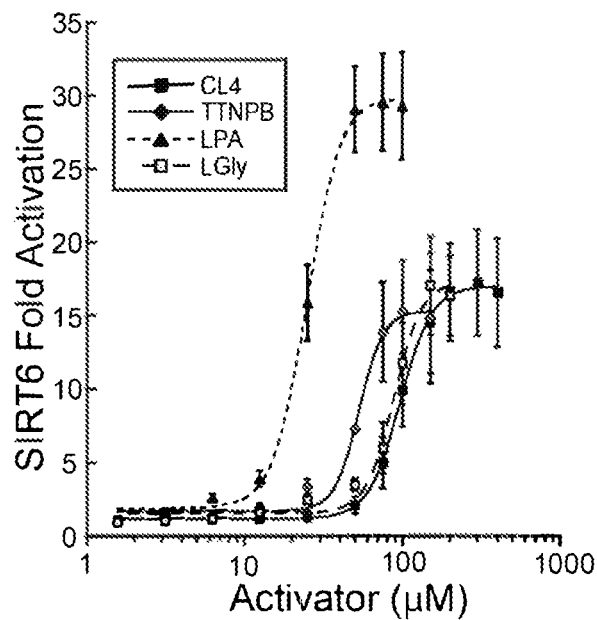

Having identified a number of novel SIRT6 activating compounds with varying structural features, LPA, L-Gly, TTNPB, and CL-4 were selected for characterization. Dose-response analysis of these compounds yielded apparent $EC_{50}$ values ranging from 25-97 μM (FIG. 1B). High concentrations of each activator (>50-300 μM) led to loss of SIRT6 activation. Due to the amphipathic nature of these compounds it was speculated that loss of activation at these high concentrations was due to micelle or aggregate formation. Using the fluorescent membrane probe, diphenylhexatriene (DPH), micelle formation was observed for LPA and L-Gly at >50 μM and >300 μM respectively, corresponding to concentrations at which activation was lost. Autofluorescence of TTNPB interfered with DPH fluorescent quantification and CL-4 was not observed to form micelles in this assay format. To test whether loss of activity was indeed the result of general micelle-like formation at high concentration, the deacetylase activity of SIRT1, SIRT2, and SIRT6 were tested in the presence of 400 μM LPA and the CL4 derivative, CL5D. All sirtuins were inhibited under these conditions suggesting a non-specific effect at high concentrations of LPA and CL5D.

Figure 1C:
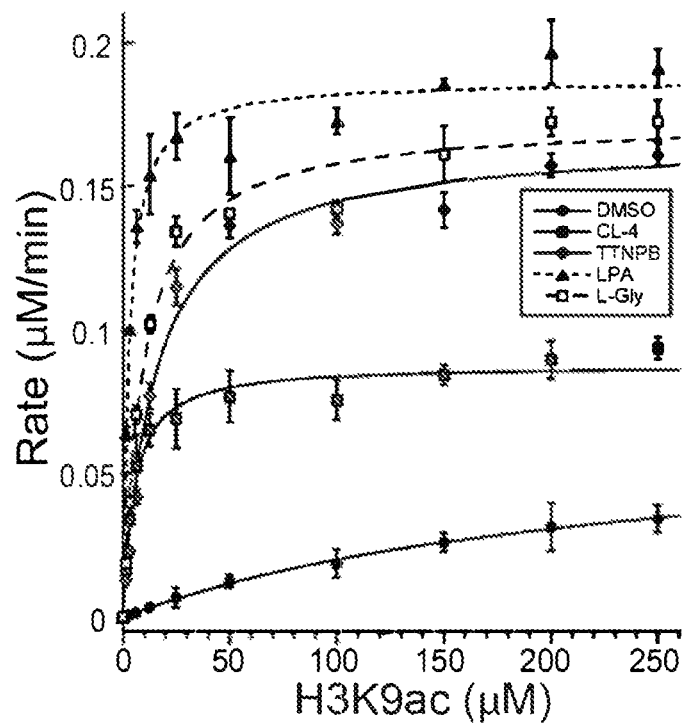

To determine which kinetic parameters are enhanced by small molecule SIRT6 activation, steady-state kinetic analyses were performed by measuring initial rates of reaction across varying H3K9ac peptide concentrations in the presence of each activator (FIG. 1C). Data were fitted to the Michaelis-Menten equation to solve for the intrinsic kinetic parameters of SIRT6 and revealed 1.4-2.9 fold increases for $k_{cat}$ and 52-312 fold increases in $k_{cat}/K_{m,\,H3K9ac}$ across the activators tested. The ratio of these two terms is used to derive $K_{m,\,H3K9ac}$, which is decreased 16-88 fold across activators (Table 2 shows dose-response and Michaelis-Menten parameters of activation by novel SIRT6 activators as determined in FIG. 1B). This strong decrease in $K_{m,H3K9ac}$ implies activation greatly improves capture of acetyl-substrate, which could be attributed to either improved substrate binding ($K_{d,\,H3K9ac}$) or in the improvement of one or more of the steps prior to the first irreversible step, release of nicotinamide. The mechanism of SIRT6 catalyzed deacylation is shown in Scheme 2: i, Substrate acyl-oxygen performs nucleophilic addition on the 1'-carbon of the nicotinamide ribose resulting in the C1-O-alkylamidate intermediate and release of nicotinamide. ii, His133 acts as a general base to facilitate the intra-molecular nucleophilic attack of the nicotinamide ribose 2'-hydroxyl on the O-alkylamidate carbon affording the 1',2'-cyclic intermediate. iii, Water catalyzed hydrolysis of the 1',2'-cyclic intermediate yields the tetrahedral intermediate. iv, Positively charged His133 donates a proton to the imino group of the tetrahedral intermediate resulting in cleavage of the C—N bond and yielding the final products. v, O-Acyl-ADPr and deaceylated lysine products are released from SIRT6.

Scheme 2

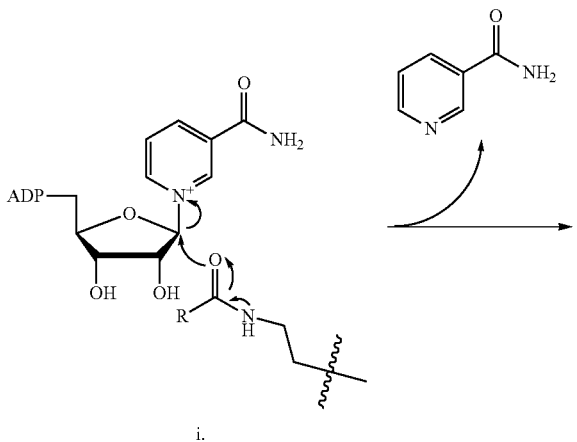

i.

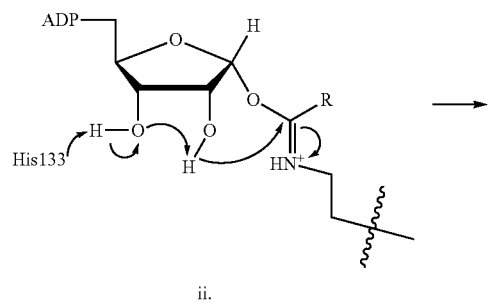

ii.

TABLE 2

| Dose response | | Michaelis-Menten parameters | | | |
|---|---|---|---|---|---|
| | $EC_{50}(μM)$ | $FA_{max}$ | | $K_{m,H3K9ac}(μM)$ | $k_{cat}(s^{-1}) \times 10^{-3}$ | $k_{cat}/K_m(M^{-1}s^{-1})$ |
| CL-4 | 97 ± 2 | 17 ± 0 2 | DMSO | 247 ± 27 | 1.1 ± 0.1 | 3.6 ± 0.5 |
| TTNPB | 53 ± 3 | 15 ± 0.8 | CL-4 | 5.2 ± 0.8 | 1.5 ± 0.3 | 284 ± 37 |
| LPA | 25 ± 1 | 30 ± 0.5 | TTNPB | 15 ± 2 | 2.8 ± 0.1 | 186 ± 20 |
| L-Gly | 88 ± 4 | 17 ± 0.8 | LPA | 2.8 ± 0.3 | 3.2 ± 0.1 | 1,126 ± 125 |
| | | | L-Gly | 9.4 ± 1.1 | 2.8 ± 0.1 | 307 + 32 |

-continued

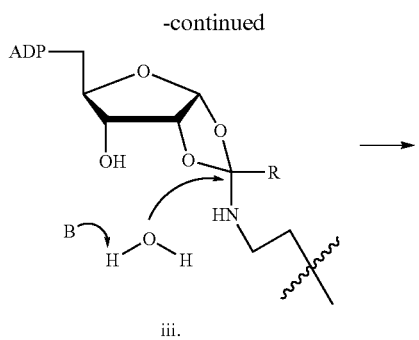

iii.

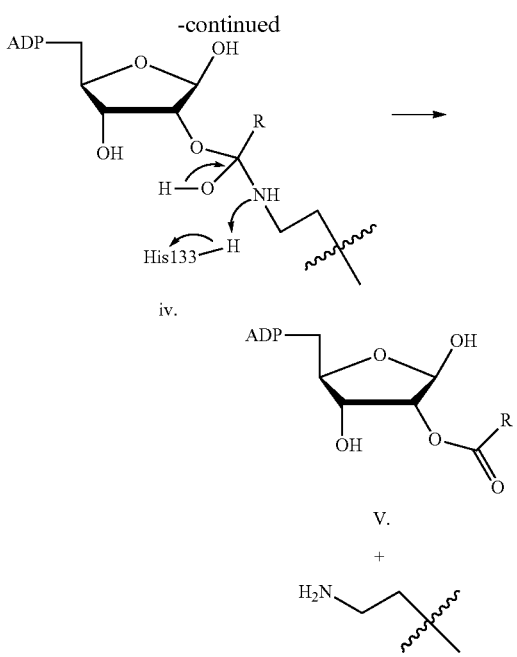

iv.

v.

+

Figure 1D:
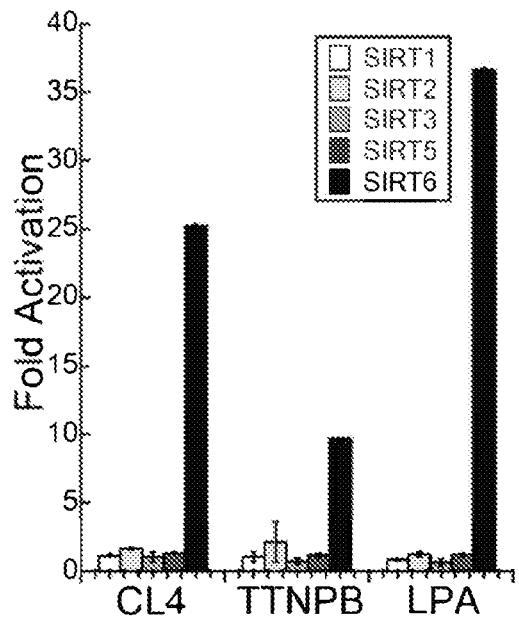

The ability of these selected small molecules to activate other mammalian sirtuins (SIRT1, SIRT2, SIRT3, and SIRT5) was evaluated. All sirtuins tested displayed measurable activity against the H3K9ac peptide. With the exception of weak stimulation (<2-fold) of SIRT2, none of the other sirtuins displayed increased activity in the presence of SIRT6 activators. Compounds CL-4, TTNPB, and LPA displayed greater than 19-fold, 4-fold, and 30-fold specificity for SIRT6 over SIRT2 respectively (FIG. 1D).

Example 3: Development and Analysis of CL5D as a SIRT6 Activator

Figure 1E:
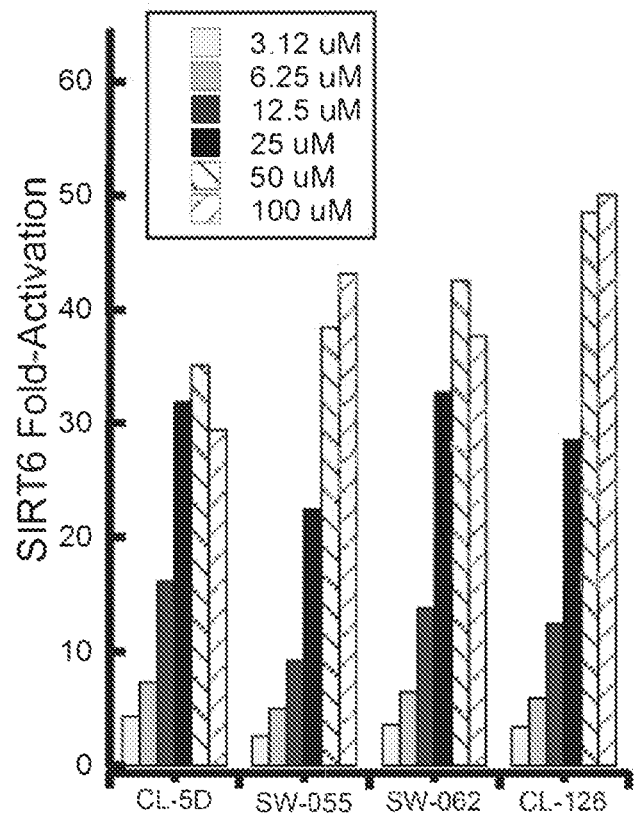
Figure 1F:
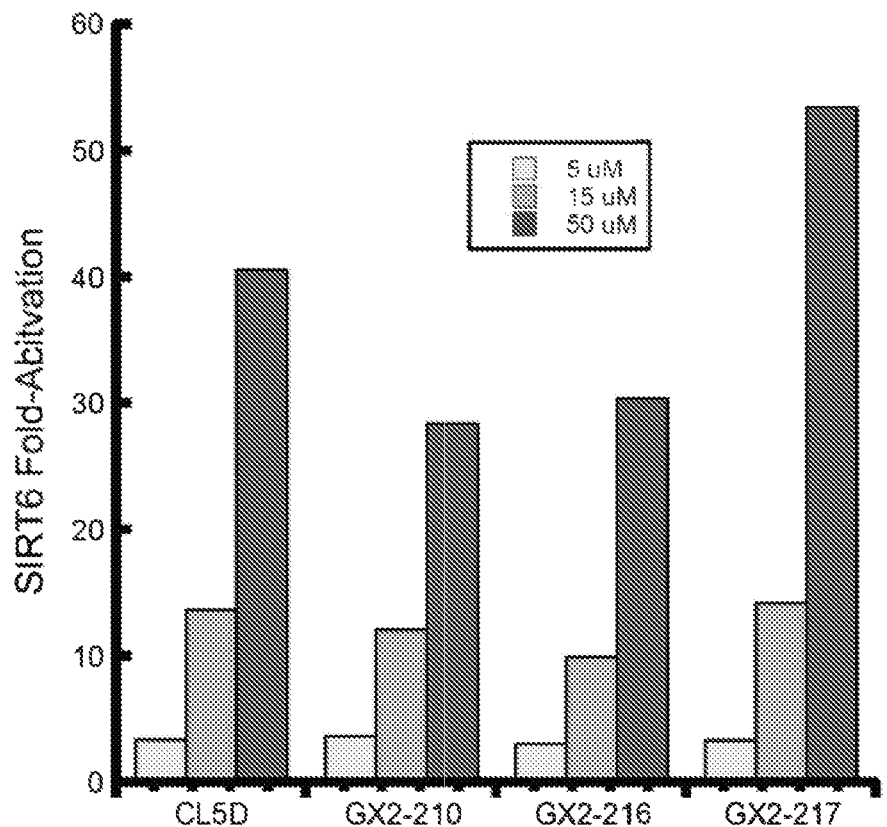

To improve potency and investigate the mechanism of activation, CL-4 was selected for chemical derivatization and structure-activity relation studies. As shown in Table 3, the concentration required to stimulate 4-fold activation of SIRT6 (1 µM) against H3K9ac (20 µM) with 0.5 mM NAD$^+$ was determined for each compound. CL-4 consists of a 4-carboxyphthalimide conjugated to a 2'-chloro-N-benzanilide. The scaffold molecule, 2-(4-benzamidophenyl)-1,3-dioxoisoindoline-5-carboxylic acid (CL-5), was synthesized without chloro groups and demonstrated no activation of SIRT6 at concentrations up to 400 µM, suggesting a critical role of halogenation (Table 3). Progressive addition of chloro groups to the scaffold restored the ability to activate SIRT6. Derivatization with a trichlorobenzoyl group led to di-substitution at the aniline nitrogen resulting in 2-(3-chloro-4-(2,4,6-trichloro-N-(2,4,6-trichlorobenzoyl)benzamido)phenyl)-1,3-dioxoisoindoline-5-carboxylic acid (CL5D). All synthetic compounds utilized in this study were confirmed by $^1$H-NMR, $^{13}$C NMR, and LC-MS (data not provided). CL5D displayed a 7-fold increased potency over CL-4 as measured by the concentration required to stimulate a 4-fold activation in SIRT6 deacetylase activity (Table 3). The only compound with substantially altered activity was the methyl-ester of CL5D which was devoid of stimulatory effects. As shown in FIGS. 1E and 1F, fold activation of SIRT6 (1 µM) against H3K9ac peptide (20 µM) in the presence of 0.5 mM NAD$^+$ varied depending on concentration of the activator compound. Taken together, the data demonstrates that electron rich terminal aromatic groups and anionic head group are important for SIRT6 stimulation in this series of compounds, but the type of anionic head group did not have a significant impact.

TABLE 3

| | | |
|---|---|---|
| | | 4-fold activation |
| CL-4 | | 35 µM |
| CL-5 | | >400 µM |
| CL-5A | | >400 µM |
| CL-5B | | 78 µM |
| CL-5C | | 120 µM |
| CL-5D | | 3 µM |

Figure 2A:
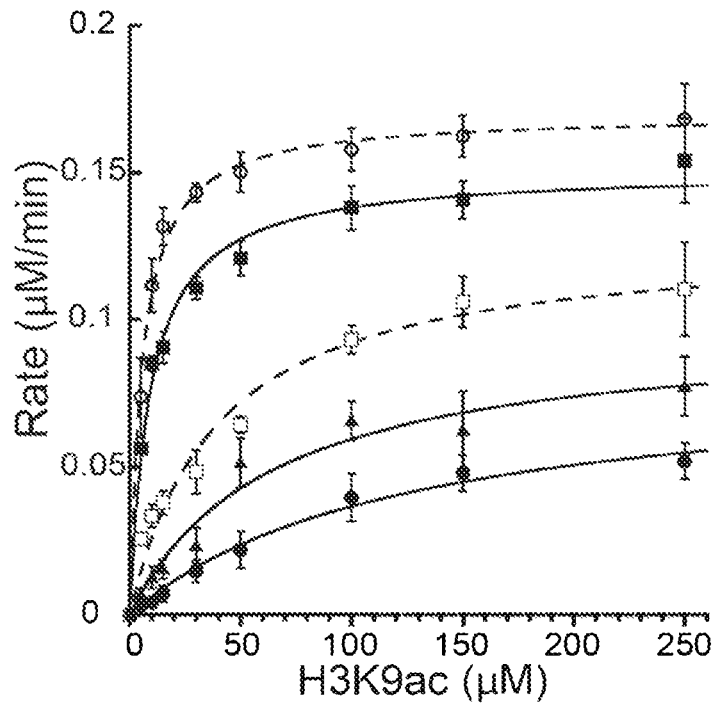
FIGS. 2A-D show results characterizing SIRT6 activator CL5D. (2A) Steady-state kinetic analysis of SIRT6 (1 μM) deacetylation was conducted with 0-250 μM H3K9ac peptide and 0.5 mM NAD$^+$ in the presence of DMSO (•), 5 μM CL5D (▲), 10 μM CL5D (□), 25 μM CL5D (■), and 50 μM CL5D (○). Data were fitted to Michaelis-Menten equation. (2B) SIRT6 demyristoylase activity determined in the presence of 0-25 μM H3K9myr peptide, 0.5 mM NAD$^+$ and 5% DMSO (•), 12.5 μM CL5D (■), 25 μM CL5D (♦), and 50 μM CL5D (▲). Data were fitted to a competitive model of inhibition with $K_i$=13.4 μM±4.8 μM. (2C) SIRT6 (1 μM) activity measured against acid extracted mammalian histones (75 μg/mL) with 0.5 mM NAD$^+$ and either 5% DMSO, 50 μM CL5, or 50 μM CL5D. (2D) H3K9ac levels were normalized to total H3 with a representative immunoblot shown. Mean values of at least three replicates are reported with error bars representing standard deviation.
Figure 2B:
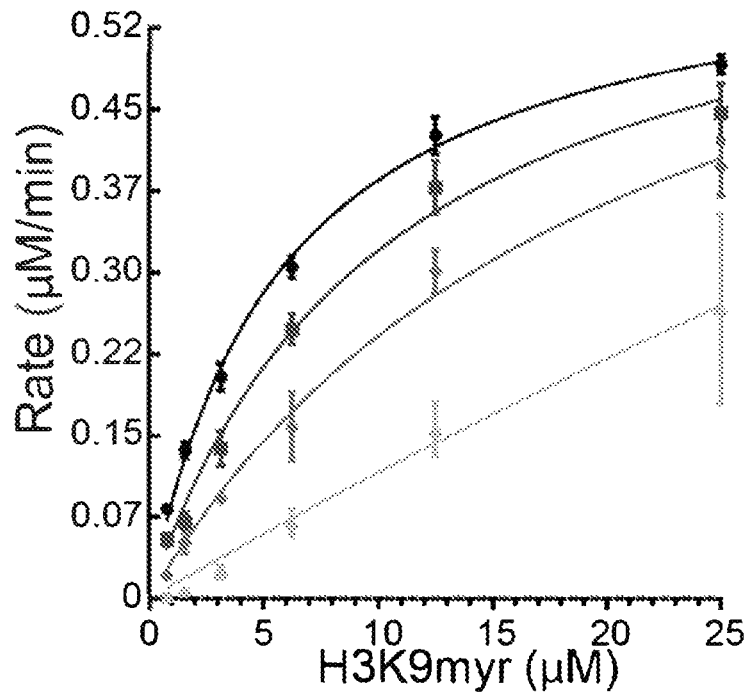
Figure 2C:
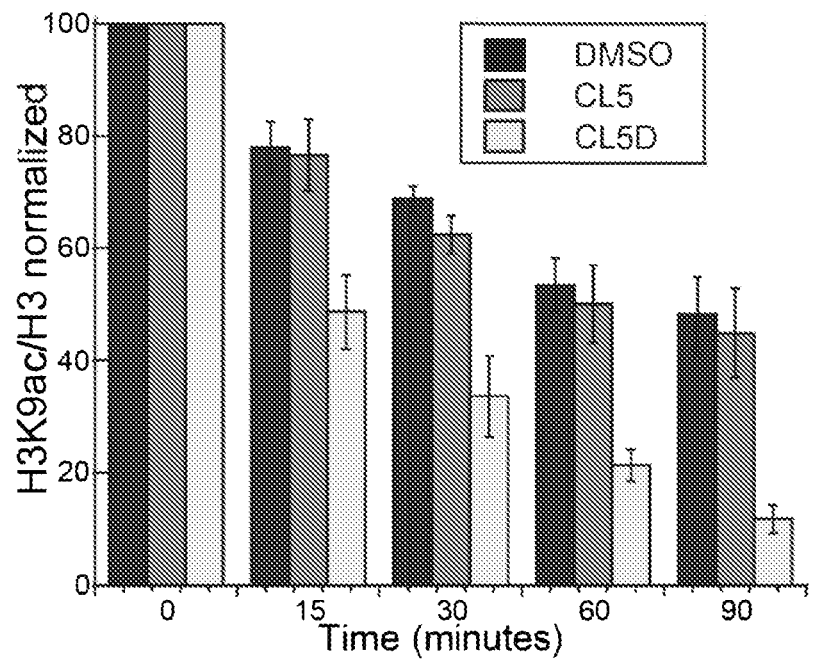
Figure 2D:
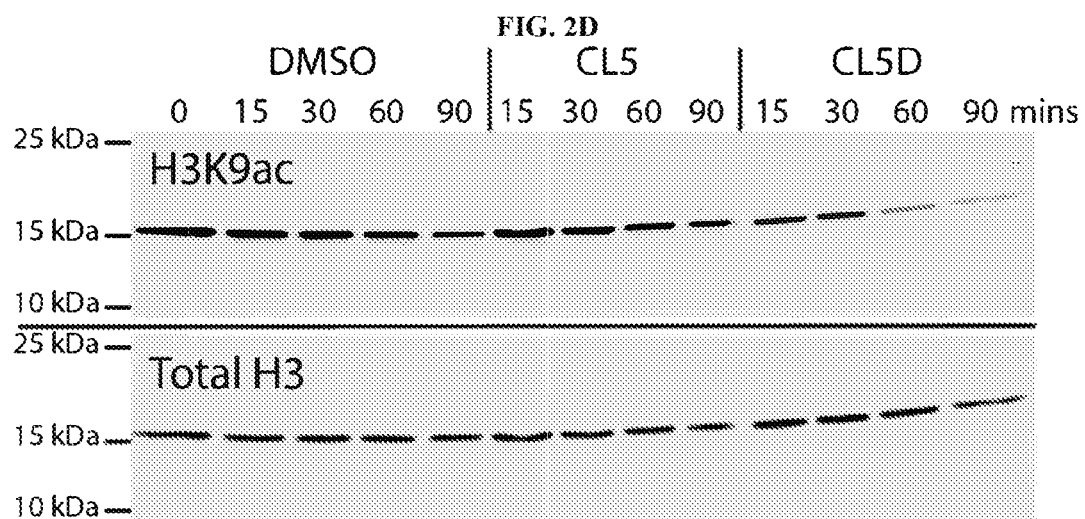

To determine which kinetic parameters are affected by CL5D, a steady-state kinetic analysis of CL5D was conducted and demonstrate a dose-dependent 50-fold increase in $k_{cat}/K_{m,H3K9ac}$ values with concurrent 2.1-fold increase in $k_{cat}$ value (FIG. 2A). CL5D activation via improved $k_{cat}/K_{m,H3K9ac}$ is consistent with the previous analysis of LPA, L-Gly, TTNPB, and CL4, suggesting that either substrate binding or a step prior to nicotinamide release is enhanced during small molecule activation. Previous studies have suggested that SIRT6 activators bind to the same hydrophobic pocket that accommodates long-acyl substrates (21). Demyristoylation assays in the presence of increasing concentrations of CL5D demonstrate competitive inhibition with a $K_i$ value of 13.4±4.8 μM (FIG. 2B). This $K_i$ value agrees well with the $EC_{50}$ value (15.5±3.2 μM). Competitive inhibition suggests that CL5D binds to the same hydrophobic pocket as long-acyl group substrates. We next tested whether CL5D would stimulate SIRT6 deacetylase activity against a full-length histone substrate. Histones were acid extracted from HEK293T cells and subjected to in vitro SIRT6 deacetylation in the presence of either CL5D or the inactive scaffold, CL5. Cells were treated with SAHA, a histone deacetylase inhibitor, to increase the relative levels of acetylated histones prior to extraction. Immunoblot analysis demonstrate time dependent deacetylation at H3K9 by SIRT6 that was stimulated by CL5D but not CL5, establishing CL5D as an activator of SIRT6 against whole histone substrate (FIG. 2C).

Example 4: Role of CL5D in Mediating SIRT6-Substrate Interaction

The initial hits selected for characterization as well as the developed activator, CL5D, stimulate SIRT6 deacetylation primarily through the improvement of $k_{cat}/K_{m,H3K9ac}$ while the $k_{cat}$ was only modestly increased. The large stimulation observed in the $k_{cat}/K_{m,H3K9ac}$ values could represent a substantial decrease in $K_{d, H3K9ac}$ value, or a rate enhancement of a catalytic step after substrate binding but before the release of nicotinamide, the first irreversible step. CL5D is subsequently utilized as a model compound for interrogating the mechanism of activation. To determine if the $K_{d, H3K9ac}$ value is directly affected by activators, we sought to measure the effect of CL5D on the binding constants for the acetylated peptide. Initial isothermal titration calorimetry (ITC) experiments yielded no measurable heats of binding of H3K9ac to SIRT6, whether CL5D was present or not (data not shown). The inability of this verified substrate to bind SIRT6 brought into question whether $NAD^+$ binding may precede that of acetyl-peptide.

Figure 3A:
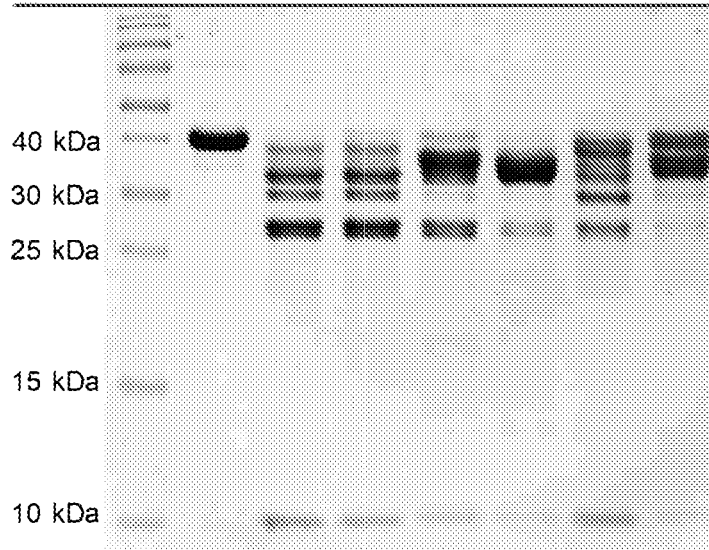
FIGS. 3A-D show that SIRT6 displays ordered binding and CL5D does not improve H3K9ac binding. (3A) Partial proteolysis of SIRT6 (0.67 mg) was conducted with subtilisin (0.67 μg) at room temperature for 25 minutes with either no additive, CL5D (50 μM), NAD$^+$ (300 μM), ADPr (300 μM), H3K9ac (100 μM), or NAD$^+$ and H3K9ac. (3B) Fluorescence polarization of N'-FAM-H3K9ac was measured in the presence of SIRT6 (0-80 μM) with or without ADPr (300 μM). Polarization in the absence of SIRT6 was subtracted from each data set with mean value reported and error bars representing standard deviation. Binding experiment ran in triplicate with mean value reported and error bars representing standard deviation. Data were fitted to a sigmoidal curve. (3C,3D) Representative ITC trace of three separate experiments obtained from 37 automatic injections (1-8 μL) of 3C; H3K9ac (0.6 mM) and ADPr (0.5 mM) into SIRT6 (15 μM) and ADPr (0.5 mM), $K_{d,HEK9ac}$=34.4±4.4 μM (N=0.70±0.14) or 3D; H3K9ac (0.6 mM), ADPr (0.5 mM), and CL5D (50 μM) into SIRT6 (15 μM), ADPr (0.5 mM), and CL5D (50 μM), $K_{d,H3K9ac}$=72.6±8.1 μM (N=0.97±0.37). Mean $K_d$ and N of three replicates reported with error representing standard deviation.

Previous mechanistic analysis of SIRT1, SIRT2, and SIRT3 demonstrated an ordered substrate binding in which acyl-lysine substrate binds prior to $NAD^+$, whereas SIRT6 was able to bind $NAD^+$ in the absence of acetylated substrate. We hypothesized that SIRT6 may display a reversed ordered binding mechanism in which $NAD^+$ binds prior to acetylated peptide substrate. To avoid the complication of enzyme turnover, we utilized ADP-ribose (ADPr) in place of $NAD^+$. ADPr is a competitive inhibitor of SIRT6 with respect to $NAD^+$ and both $NAD^+$ and ADPr have been shown to bind to SIRT6 with similar affinities. We then investigated the ability of $NAD^+$ and ADPr to induce SIRT6 conformational changes. Changes in sensitivity to partial proteolysis by subtillisin were monitored in the presence of ADPr, $NAD^+$, or H3K9ac (FIG. 3A). Partial protection from proteolysis was observed under saturating conditions of either $NAD^+$ or ADPr, when compared to no ligand controls. Addition of 100 μM H3K9ac provided minimal protection from proteolysis, however the addition of both H3K9ac and ADPr increased protection relative to ADPr alone. These results suggest that ADPr and $NAD^+$ induce a similar conformational change in SIRT6, and importantly show that ADPr can be used as an $NAD^+$ binding surrogate that can co-occupy SIRT6 with H3K9ac in order to investigate substrate binding under non-catalytic conditions.

Figure 3B:
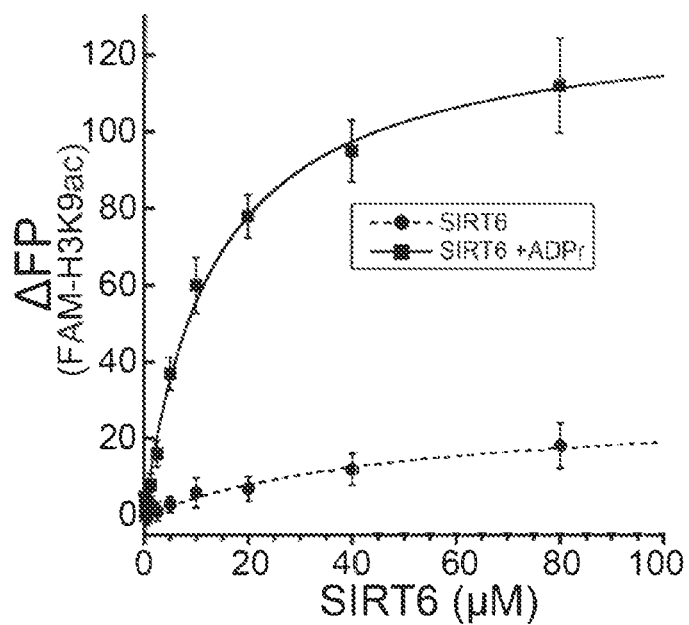
Figure 3C:
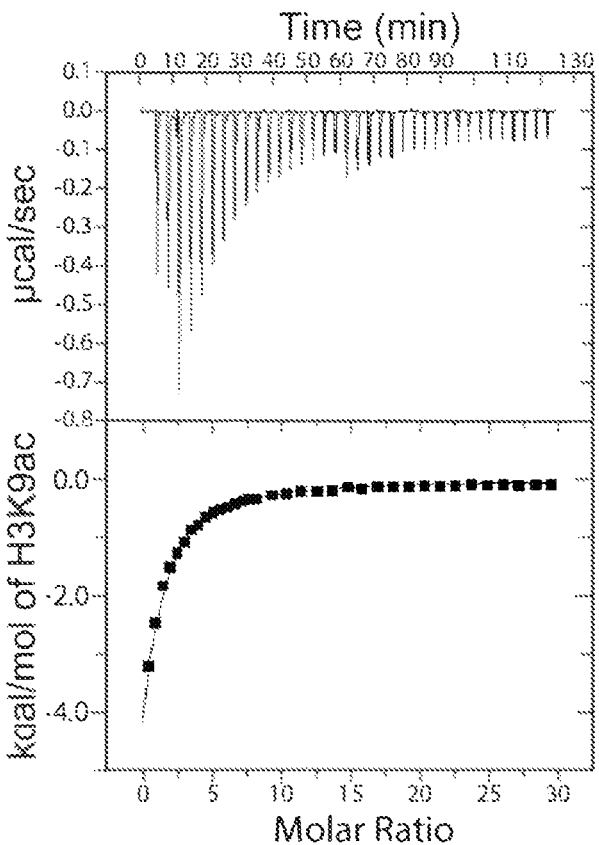

To determine whether ADPr binding must precede acetylated substrate binding, we first synthesized a fluorescein labeled H3K9ac peptide (FAM-H3K9ac) amenable for fluorescent polarization (FP) binding assays. Binding of FAM-H3K9ac to SIRT6 was then assessed by FP in the presence and absence of saturating amounts of ADPr (FIG. 3B). These results demonstrate efficient binding of FAM-H3K9ac only in the presence of ADPr, and were confirmed via ITC, where the addition of ADPr allowed for quantification of H3K9ac peptide binding with a measured $K_{d,H3K9ac}$ of 34.4±4.4 μM (FIG. 3C).

Figure 3D:
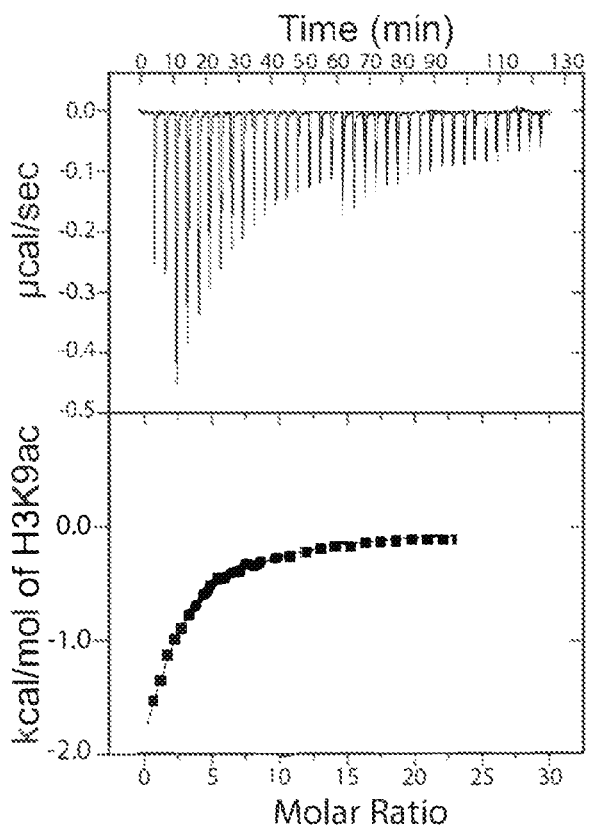

To address our initial question of whether activators enhance $K_{d,H3K9ac}$, ITC was used to determine the binding constant of H3K9ac in the presence of CL5D and requisite ADPr. Quantification yielded a $K_{d,H3K9ac}$ of 72.6±8.1 μM in the presence of CL5D (FIG. 3D). Together, these data demonstrate that SIRT6 displays ordered binding in which $NAD^+$ binding precedes substrate binding and that the mechanism of SIRT6 activation does not involve improved binding affinity for acetyl-substrate. These results suggest that the greatest rate-enhancement by small molecule activation involves a catalytic step(s) after substrate binding but prior to nicotinamide dissociation.

Example 5: Identification of Non-Activatable SIRT6 R65A Mutant

Figure 6A:
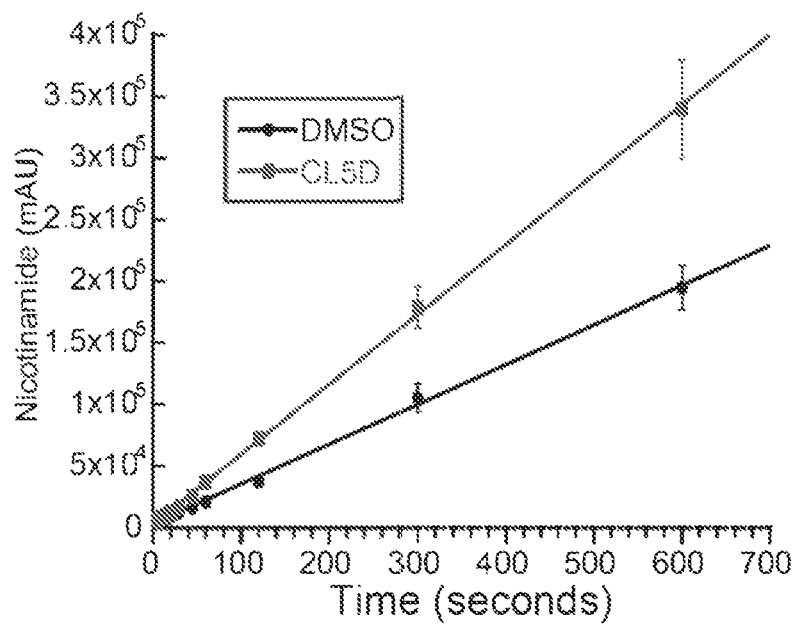
FIGS. 6A-D show R65 facilitates conformational change during enhanced catalysis. (6A) SIRT6 (10 μM) was pre-mixed with 400 μM H3K9ac peptide prior to reaction initiation with 500 μM NAD$^+$. Reactions were allowed to proceed for 10-600 seconds prior to HPLC quantification of nicotinamide. Reactions were performed in duplicate with average value plotted and error bars representing standard deviation. These kinetics were also performed in duplicate with reversed order of substrate addition. (6B) Partial proteolysis of SIRT6 WT or R65A (0.67 mg) was conducted with subtillisin (0.67 μg) at room temperature for 25 minutes with either no additive, NAD$^+$ (300 or ADPr (300 (6C) Melting temperatures determined for SIRT6 WT and R65A (10 μM) with and without NAD$^+$ (1 mM). Thermal denaturation was performed in triplicate with mean value reported. (6D) The general kinetic scheme of sirtuins has been previously proposed (5), however here we propose an updated deacylation scheme for SIRT6. First, ordered binding in which SIRT6 binds NAD$^+$ prior to acyl-substrate. Subsequent to substrate binding we include a conformational step that is improved during enhanced catalysis in an R65-dependent manner.
Figure 6B:
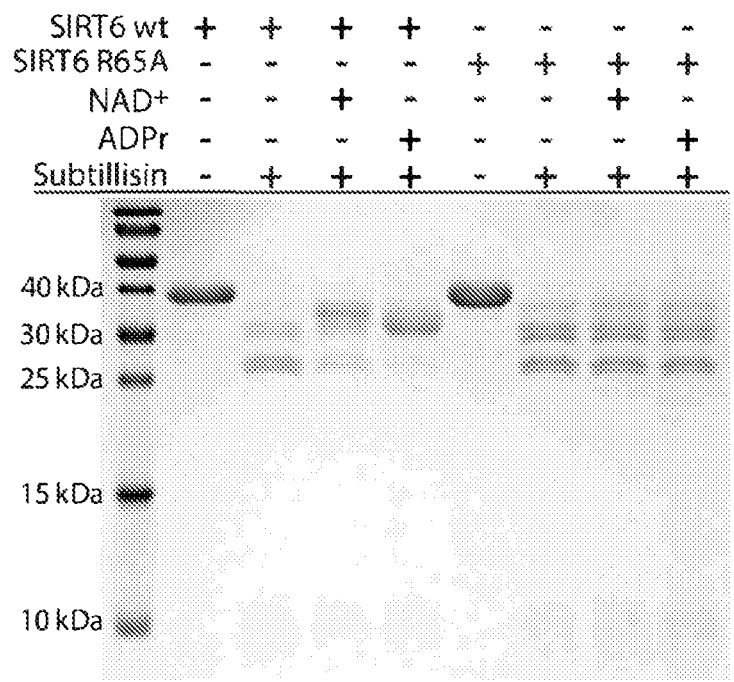
Figure 6C:
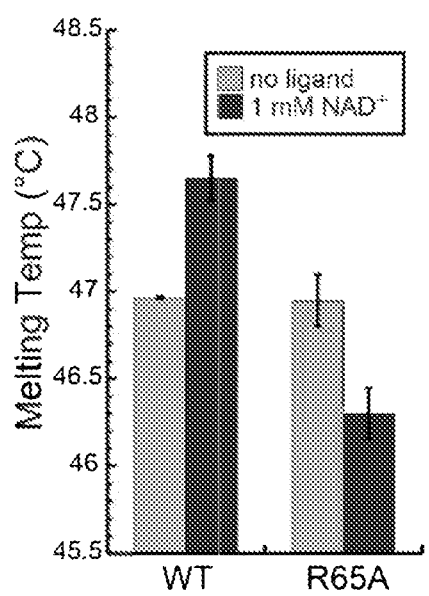
Figure 6D:
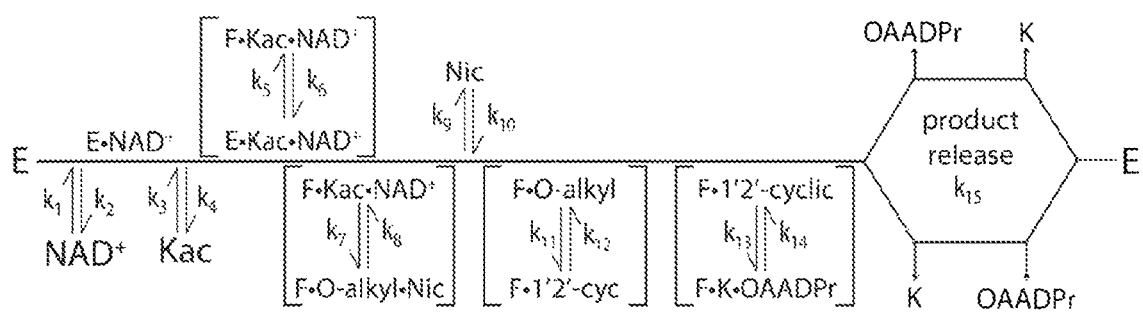

Activation of deacetylation by CL5D is primarily driven through improvement of the $k_{cat}/K_{m,H3K9ac}$ parameter which suggests the enhancement of a catalytic step(s) including or prior to nicotinamide release. These steps include the rate of alkylamidate formation or a potential slow conformational change of SIRT6 subsequent to substrate binding (FIG. 6D). The rate of alkylamidate formation for various sirtuins has previously been determined utilizing single-turnover kinetics in which sub-stoichiometric amounts of substrate are saturated with enzyme (5). However, the prohibitively high concentration (~1-2 mM) of SIRT6 required to saturate H3K9ac peptide substrate in rapid quench experiments precludes the use of single turnover kinetics to interrogate the rate of alkylamidate formation during enhanced deacetylation.

Figure 4A:
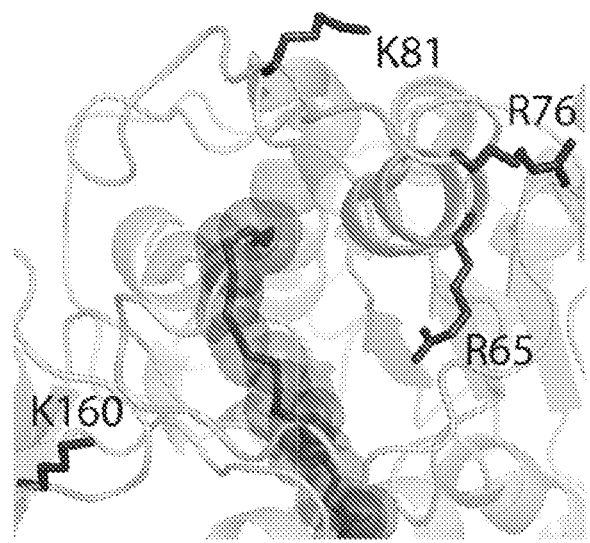
FIGS. 4A-D show identification of the non-activatable R65A SIRT6 mutant. (4A) Arginine and lysine residues (stick representation) selected for mutation due to proximity to myristoyl binding pocket (sticks with transparent spheres) and active site pocket (PDB: 3ZG6). (4B) Initial rates of SIRT6 WT and R65A (1 μM) were measured in triplicate over a range of H3K9ac substrate (0-250 μM) in the presence or absence of CL5D (50 μM) and mean values fitted to Michaelis-Menten equation with error bars representing standard deviation. (4C) R65 is positioned on the NAD$^+$-binding loop and makes interactions with nicotinamide ribose and pyrophosphate of ADPr. Structure of SIRT6 (transparent grey ribbon) liganded with H3K9myr (sticks with spheres) and ADPr (medium grey). The NAD$^+$ binding loop of SIRT6 (sticks in light grey) contains R65 (sticks in dark grey) at the kink of a loop and making hydrogen bonds with the adenosine ribose and pyrophosphate of ADPr. (PDB: 3ZG6) (4D) SIRT6 WT and R65A (1 μM) demyristoylase activity was measured in the presence of 20 μM H3K9myr peptide substrate. Mean value of at least three replicates reported.
Figure 4B:
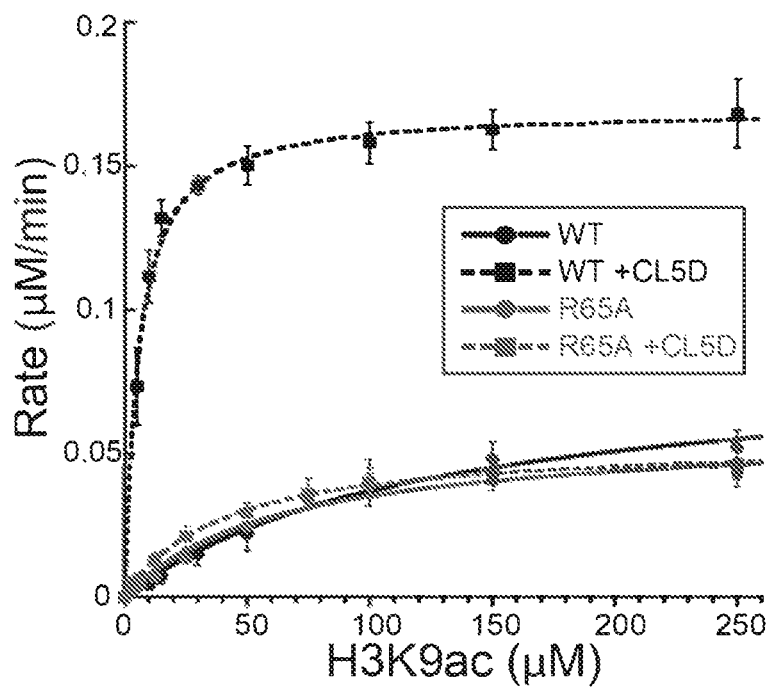

In an effort to identify residues critical for the enhancement of SIRT6 catalysis, we screened several mutants (R76A, R65A, K81A, and K160A) and assessed the ability of these variants to be activated by small molecules (FIG. 4A). Steady-state rates of deacetylation of SIRT6 WT, R76A, K81A, K160A, and R65A (1 μM) against H3K9ac (40 μM) with or without CL5D (50 μM) Reactions were performed in triplicate for 25 minutes with mean value reported and error representing standard deviation of runs. Subsequent analysis of these mutants reveal that all retain base level deacetylase activity, however, only SIRT6 R65A cannot be activated by CL5D (Table 4). Steady-state kinetic analysis of SIRT6 R65A confirmed the inability to be stimulated by CL5D over a large range of H3K9ac peptide substrate concentrations (FIG. 4B).

TABLE 4

| Mutant | Rate$_{DMSO}$ (μM/min) | Rate$_{CL5D}$ (μM/min) | Fold Activation |
|---|---|---|---|
| WT | 0.013 ± 0.0006 | 0.164 ± 0.008 | 12.9 |
| R76A | 0.016 ± 0.0004 | 0.155 ± 0.004 | 9.8 |

TABLE 4-continued

| Mutant | Rate$_{DMSO}$ (µM/min) | Rate$_{CLSD}$ (µM/min) | Fold Activation |
|---|---|---|---|
| K81A | 0.014 ± 0.0005 | 0.125 ± 0.003 | 8.6 |
| K160A | 0.009 ± 0.0006 | 0.126 ± 0.006 | 13.5 |
| R65A | 0.010 ± 0.0004 | 0.014 ± 0.004 | 1.3 |

Figure 4C:
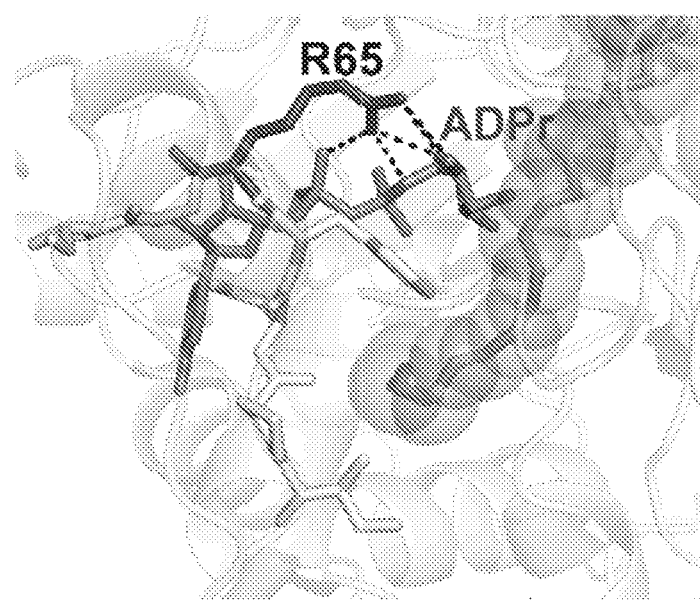

Structural analysis reveals that R65 is positioned on a kinked turn of the NAD$^+$-binding loop and makes extensive contacts with the adenosine ribose and pyrophosphate of ADPr (FIG. 4C). Previous studies have identified loss-of-function mutations of a neighboring aspartate to either tyrosine or histidine (D63Y/H). SIRT6 D63Y was selected for in naturally occurring human tumors, and D63H was identified as a driving mutation in four consecutive late fetal losses of a consanguineous couple (11,32). These studies and our analysis suggest that SIRT6 catalysis is particularly sensitive to mutation of the NAD$^+$ binding loop.

Previously, SIRT6 R65 was reported to be critical for deacetylation in cells, but a detailed mechanistic understanding was never provided (33). Here, in vitro analysis reveals that SIRT6 R65A lacks the ability to be stimulated towards deacetylation by small molecule activators. Together, this suggests a critical role for endogenous SIRT6 activation.

Figure 4D:
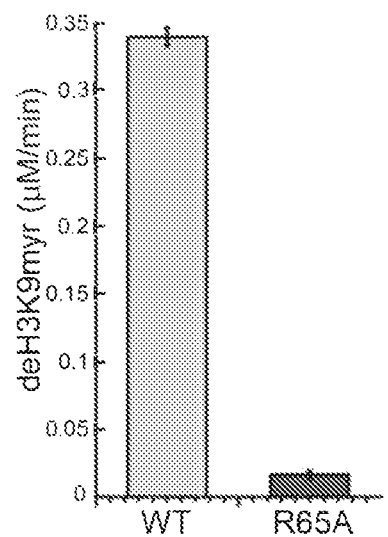

SIRT6 is a more efficient long-chain deacylase than deacetylase, therefore the inability of the R65A mutant to perform activated deacetylation led us to ask whether this mutant was also a poorer demyristoylase (21,35). Remarkably, SIRT6 R65A deacylase activity against H3K9myr peptide is greatly reduced relative to wild type (FIG. 4D). The inability of the R65A variant to perform activated deacetylation or efficient demyristoylation suggests a common allosteric role of R65 in mediating enhanced SIRT6 catalysis. Therefore, SIRT6 R65A is utilized as a tool in subsequent analyses to investigate which catalytic steps are affected during enhanced catalysis.

Example 6: Characterization of SIRT6 R65A Catalysis and Binding Parameters

Figure 5A:
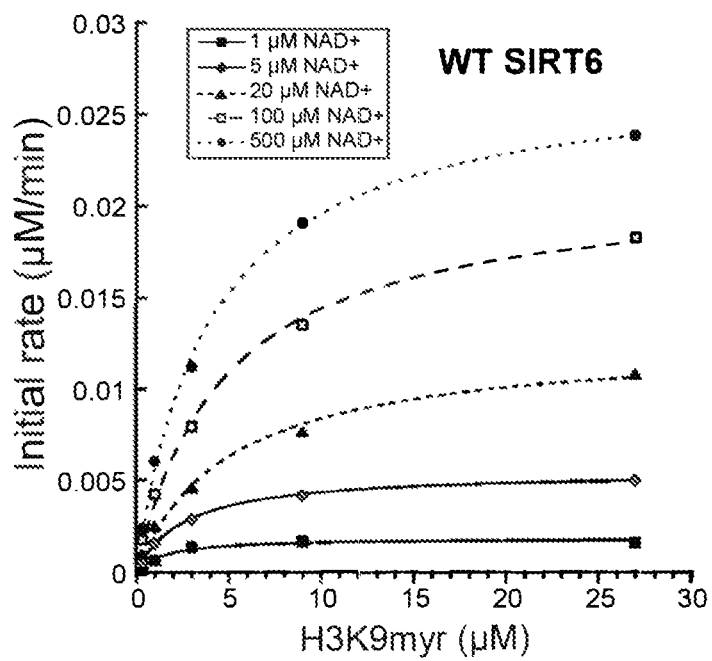
FIGS. 5A-D show kinetic analyses of SIRT6 wild type and R65A demyristoylation. (5A, 5B) Steady-state demyristoylation rates of H3K9myr (0.33-27 μM) by SIRT6 WT and R65A (1 μM) were determined in the presence of 1-500 μM NAD$^+$. These experiments were repeated on different days, with one set of representative curves with fits shown. Results from duplicate experiments are tabulated in Table 5. The data were fitted to an ordered sequential bi-substrate equation to derive $V_{max}$, $K_{m,\ H3K9myr}$, $K_{m,\ NAD+}$, $K_{d,\ H3K9myr}$, and $K_{d,NAD+}$. (5C, 5D) Pre-steady state single-turnover kinetics of SIRT6 WT and R65A (18 μM) were determined with 300 μM NAD$^+$ in the presence of 5 μM H3K9myr. Nicotinamide and demyristoylated product were monitored by HPLC and curves were fitted to a single exponential to determine first order rate constants. Mean value of three replicates plotted with error bars representing standard deviation.
Figure 5B:
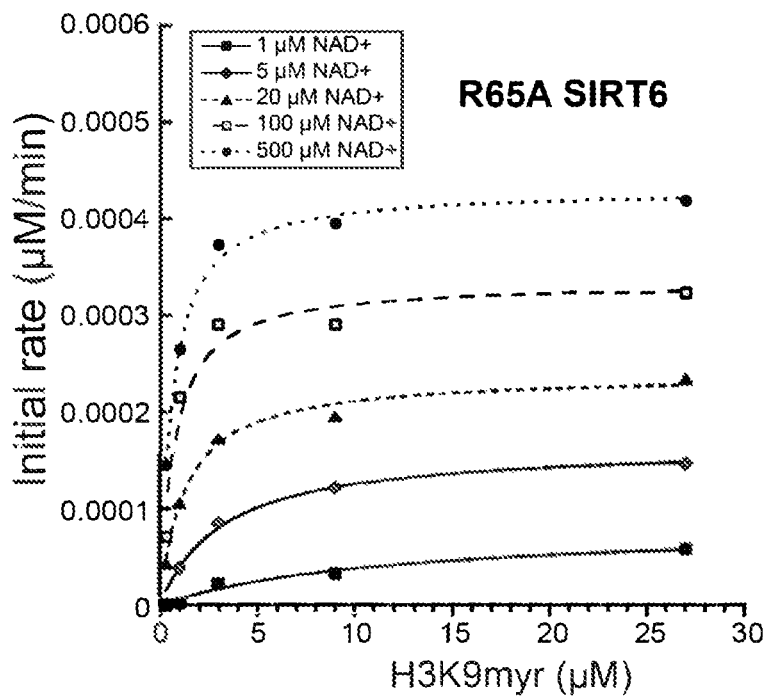

Having demonstrated that R65 facilitates enhanced SIRT6 catalysis we performed global steady-state analysis of SIRT6 WT and R65A demyristoylation to isolate kinetic parameters associated with enhanced catalysis. Bi-substrate kinetic analyses on wild-type and R65A SIRT6 were performed by measuring initial turnover rates under a matrix of H3K9myr peptide and NAD$^+$ concentrations (FIGS. 5A,B). Through fitting to a sequential bi-substrate reaction equation, values for $k_{cat}$, $K_{d, NAD+}$, $K_{d, H3K9myr}$, $K_{m, NAD+}$, $K_{m, H3K9myr}$ were determined, and the fold-increase in each parameter observed in wild-type vs R65A SIRT6 was calculated (Table 5). The R65A mutant enzyme yielded a 65-fold decrease in $k_{cat}$ and a 8.0-fold decrease in $k_{cat}/K_{m, H3K9myr}$ that cannot be fully accounted for by the 1.2-fold decrease in $K_{d,H3K9myr}$. Fluorescence polarization was used to determine the effect of the R65A on the binding of a fluorescein-labeled H3K9myr peptide. The R65A variant demonstrated an improved $K_{d,FAM-H3K9myr}$ over

TABLE 5

|  | R65A | WT | Avg. Fold increase |
|---|---|---|---|
| $K_{cat}$ (s$^{-1}$) | 1.0 × 10$^{-4}$ ± 3.9 × 10$^{-6}$ | 7.0 × 10$^{-3}$ ± 3.4 × 10$^{-4}$ | 65.3 |
|  | (9.4 × 10$^{-5}$ ± 3.16 × 10$^{-6}$) | (5.9 × 10$^{-3}$ ± 3.2 × 10$^{-4}$) |  |
| $K_{M, H3K9myr}$ (µM) | 0.47 ± 0.11 | 4.2 ± 0.65 | 8.2 |
|  | (0.45 ± 0.11) | (4.0 ± 0.68) |  |
| $K_{M, NAD+}$ (µM) | 11 ± 2.4 | 25 ± 5.1 | 2.1 |
|  | (12 ± 2.3) | (22 ± 4.9) |  |
| $K_{d, H3K9myr}$ (µM) | 3.9 ± 17 | 5.0 ± 2.5 | 1.2 |
|  | (4.2 ± 16) | (4.6 ± 2.4) |  |
| $K_{d, NAD+}$ (µM) | 90 ± 40 | 30 ± 13 | 0.30 |
|  | (96 ± 42) | (26 ± 14) |  |
| $K_{cat}/K_{M, H3K9myr}$ (s$^{-1}$*M$^{-1}$) | 220 ± 49 | 1,700 ± 197 | 8.0 |
|  | (177 ± 35) | (1,470 ± 189) |  |
| $K_{cat}/K_{M, NAD+}$ (s$^{-1}$M$^{-1}$) | 9.4 ± 1.9 | 280 ± 50 | 31.6 |
|  | (78 ± 14) | (259 ± 47) |  |
| Alkylimidate formation (s$^{-1}$) | 0.054 ± 0.003 | 0.076 ± 0.006 | 1.4 |
| 1'2'-bicyclic formation (s$^{-1}$) | 0.0021 ± 0.0001 | 0.033 ± 0.002 | 15.7 | wild type SIRT6 (0.51±0.04 µM and 2.1±0.13 µM respectively), which is in agreement with the $K_{d,H3K9myr}$ values determined by bi-substrate kinetic analysis (3.9±1.7 µM and 5.0±2.5 µM respectively). An effect on $k_{cat}/K_{m,H3K9myr}$ not accounted for by binding of substrates is in agreement with enhanced catalysis involving a step(s) after substrate binding but prior to the release of nicotinamide. Importantly, this affected step(s) is mediated by R65. The large decrease in the $k_{cat}$ of demyristoylation for SIRT6 R65A suggests that a step including or subsequent to the formation of the 1',2'-bicyclic intermediate, which is not reflected in $k_{cat}/K_{m, H3K9myr}$, is impaired (Scheme 2). This impaired step is unique to demyristoylation, as SIRT6 R65A does not demonstrate impaired $k_{cat}$ of deacetylation relative to WT, suggesting that the rate-limiting steps of deacetylation and demyristoylation differ in the R65A mutant. From prior work on a sirtuin homolog HST2, product release was limiting for overall $k_{cat}$ values (35). Accordingly, the release of the hydrophobic O-myristoyl-ADPr product may become rate limiting for SIRT6 R65A mediated demyristoylation.

Together, these results suggest that R65 mediates a catalytic step reflected in the $k_{cat}/K_{m,H3K9myr}$ of enhanced deacylation after substrate binding but prior to the release of nicotinamide (FIG. 6D). As such, the $k_{cat}/K_{m,H3K9my}$ might reflect the rate of alkylamidate formation or a conformational change subsequent to substrate binding.

Example 7: Single Turnover Kinetic Analysis of SIRT6 R65A Demyristoylation

Changes in catalytic efficiency ($k_{cat}/K_m$) reflect the rates of substrate binding and all subsequent steps through the first irreversible step, the release of nicotinamide. The steady-state reaction parameters of wild-type and R65A SIRT6 revealed differences in catalytic efficiency during enhanced SIRT6 catalysis.

Figure 5C:
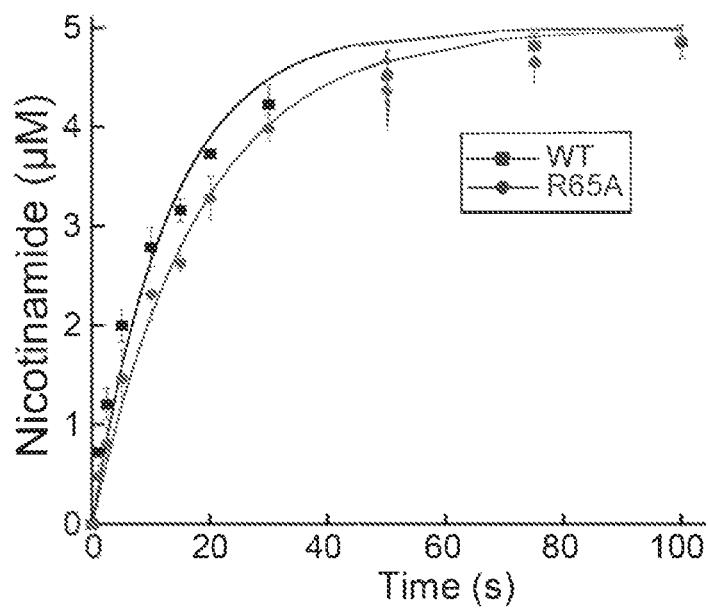
Figure 5D:
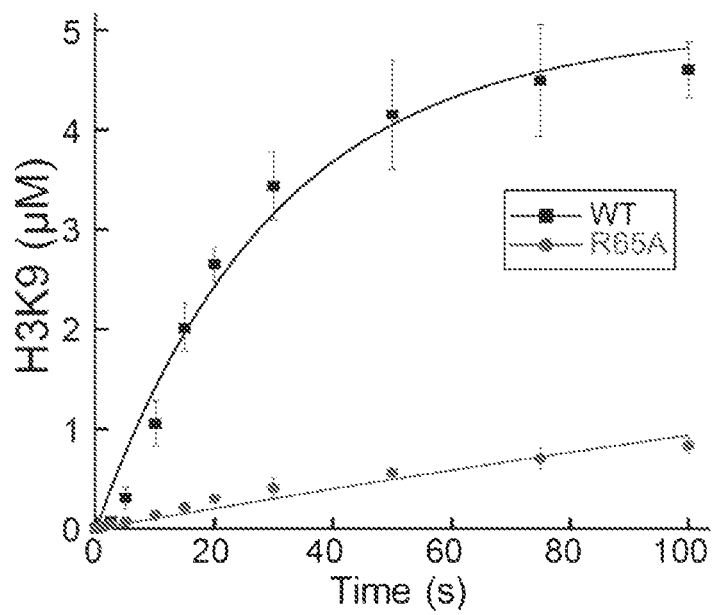

To provide mechanistic details about the individual steps during enhanced catalysis a single-turnover, rapid-quench kinetic analysis was performed to monitor the rates of alkylamidate and 1',2'-bicyclic intermediate formation. Assays were performed with limiting myristoyl-substrate, permitting only a single turnover of the enzyme. Wild-type and R65A SIRT6 (18 µM) were incubated with saturating NAD$^+$ and 5 µM myristoyl-peptide. Following rapid acid-quenching (1-100 seconds), nicotinamide and demyristoylated peptide were quantified by HPLC and rates of each were determined using a single-exponential fit (FIGS. 5C,D). In this analysis, the formation of the alkylamidate occurs concomitant with the formation of nicotinamide which was detected and used to quantify this rate (Step i. Scheme 2). The subsequent step, formation of the 1',2'-cyclic intermediate (Step ii. Scheme 2), results in an acid labile intermediate that decomposes following acid quench to form deacylated peptide which was detected and used to quantify this rate (Table 5). The rate of alkylamidate formation between wild-type and R65A (0.075 s$^{-1}$ and 0.054 s$^{-1}$ respectively) was similar; however the rate of 1',2'-cyclic formation for R65A was reduced 16 fold compared to wild-type (0.002 s$^{-1}$ and 0.033 s$^{-1}$ respectively). These data implicate R65 in facilitating the formation of the 1',2'-cyclic intermediate.

Despite the fact that the R65A mutant has an impaired rate of 1',2'-cyclic formation (0.002 s$^{-1}$) (Step ii. Scheme 2), this rate is still an order of magnitude greater than the steady-state $k_{cat}$ value of demyristoylation (0.0001 s$^{-1}$) suggesting a subsequent non-reversible catalytic step or product release becomes rate limiting during SIRT6 R65A demyristoylation. Given that $k_{cat}$ of SIRT6 R65A demyristoylation (0.0001 s$^{-1}$) is an order of magnitude slower than the corresponding $k_{cat}$ of deacetylation (0.001 s$^{-1}$), it is likely that product release of the bulky hydrophobic 0-myristoyl-ADPr becomes rate limiting for the R65A mutant.

The non-activatable R65A mutant shows a minimal 1.4 fold decrease in the rate of alkylamidate formation (Step i. Scheme 2), the only chemical step reflected in $k_{cat}/K_{m,H3K9myr}$. This modest involvement of R65 in facilitating alkylamidate formation is insufficient to explain the decrease in $k_{cat}/K_{m,H3K9myr}$ compared to wild type SIRT6 and suggests that enhanced catalysis is nearly independent of changes to the rate of alkylamidate formation. This kinetic data can be explained by the existence of additional non-chemical steps that precede alkylamidate formation. We propose a conformational change mediated by R65 that drives efficient demyristoylation of wild type SIRT6. Kinetic analysis of deacetylation is required to evaluate whether activated deacetylation is also driven by the improvement of a non-chemical step.

Example 8: Evidence for Slow Conformational Change after Substrate Binding

Enhancement of deacetylation by CL5D improves $k_{cat}/K_{m,H3K9ac}$ for SIRT6 by 50 fold and this improvement is absent from the R65A variant. To further dissect the catalytic step(s) in $k_{cat}/K_{m,H3K9ac}$ that are enhanced in the presence of activator, reaction conditions were set up to identify the existence of product 'bursts' during the first catalytic turnover. High concentrations of SIRT6 (10 µM) in the presence of 400 µM H3K9ac peptide were rapidly mixed with 500 µM NAD$^+$, and after an acid quench at different times, the products nicotinamide and deacetylated peptide were resolved and quantified by HPLC. Plotting the products formed as a function of time revealed no product bursts (FIG. 6A), only a linear rate that was in agreement with steady-state $k_{cat}$ values, and a consistent 1.8 fold rate enhancement in the presence of CL5D. The order of substrate mixing had no effect on the product curves. The lack of a nicotinamide burst suggests that a step after binding but before the first chemical step is relatively slow. Such a rate-determining step prior to the first catalytic step is likely to be a slow conformational step, and the fact that all tested activators display a large increase in $k_{cat}/K_{m,H3K9ac}$ suggests that activators enhance this step.

Lack of product burst suggests that the rate-limiting step of deacetylation occurs prior to the release of nicotinamide and is therefore reflected in the $k_{cat}/K_{m,H3K9ac}$ allowing this term to be modeled using an example equation provided by Johnson et al. (36). This equation includes a conformational step subsequent to substrate binding followed by an irreversible step, the last rate encompassed in $k_{cat}/K_{m,H3K9ac}$ and reflective of the rate of alkylamidate formation in our analysis. Modeling suggests that, for example, a 100 fold increase in the forward rate of conformational rate coupled with a 6 fold decrease in the reverse rate would be sufficient to improve $k_{cat}/K_{m,H3K9ac}$ from 2.2 M$^{-1}$s$^{-1}$ to 554 M$^{-1}$s$^{-1}$ in agreement with the empirically measured improvement by small molecule activation from 3.6 M$^{-1}$s$^{-1}$ to 511 M$^{-1}$s$^{-1}$. Further kinetic modeling of the $k_{cat}/K_{m,H3K9ac}$ term demonstrates that improvements to the rate of alkylamidate formation sufficient to drive the observed activation would necessitate a rate ~150 fold faster than that of $k_{cat}$. Such a rate improvement would have yielded a burst in nicotinamide production suggesting that an enhancement to a conformational rate is more likely. Together these analyses demonstrate that small molecule activation cannot be accounted for solely by an improvement in alkylamidate formation. Instead, activated deacetylation by small molecule binding involves the improved equilibrium of a conformational change that is prior to the first chemical step and facilitated by R65.

Example 9: Involvement of R65 in SIRT6 Conformation

To provide evidence that R65 facilitates conformational changes of SIRT6, the sensitivity of the R65A variant to limited proteolysis was assessed in the presence of 300 µM NAD$^+$ or ADPr. Unlike wild type enzyme in the presence of cofactor, the R65A variant lacked protection from proteolysis in the presence of NAD$^+$ or ADPr, suggesting that the R65A variant is deficient in the ability to adopt the conformational change (FIG. 6B). To determine if proteolytic protection of wild type SIRT6 by cofactors is associated with an increased stability of the enzyme, thermal denaturation assays were conducted, yielding melting temperature values ($T_m$) of wild type and R65A proteins in the presence of 1 mM NAD$^+$. Addition of NAD$^+$ led to an increase of wild type SIRT6 $T_m$ by 0.7° C., whereas the $T_m$ of SIRT6 R65A was decreased by 0.6° C. (FIG. 6C). The destabilization of SIRT6 R65A in the presence of NAD$^+$ suggests that the enzyme still binds cofactor, in agreement with the bisubstrate kinetic analysis (Table 5).

Collectively, the detailed kinetic and biochemical analyses strongly suggest that SIRT6 activation of deacetylation by the small molecules revealed in this study occurs primarily through an enhancement of a slow conformational change after substrate binding that is mediated by R65. To reflect these new results, an updated kinetic model of SIRT6 catalysis includes this conformational step (FIG. 6D). Efficient long-chain deacylation is also dependent on R65, suggesting that long-chain acyl substrates facilitate this conformational change leading to enhanced catalysis. Furthermore, the R65A variant displays a decreased $k_{cat}$ of demyristoylation below that of deacetylation, suggesting that R65 also facilitates a conformational step required for release of the bulky O-myristoyl-ADPr product.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions, or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third, and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

All patents, patent applications, provisional applications, and publications referred to or cited herein are incorporated by reference in their entireties, including all figures and tables, to the extent they are not inconsistent with the explicit teachings of this specification.

The invention claimed is:

1. A compound of Formula I,

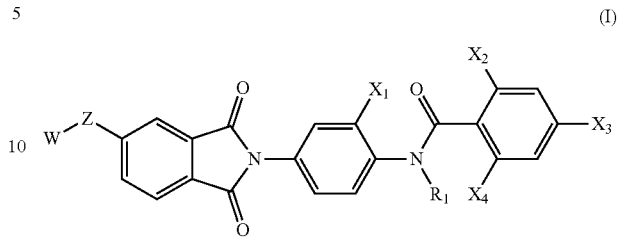

and pharmaceutically acceptable salts thereof, wherein

Z is absent or is $C(O)NH(CH_2)_nCH(R^4)$;

W is selected from a carboxyl, phosphoric acid, sulfuric acid, or ester group;

$X^1$ is H, F, Cl, or Br;

each of $X^2$, $X^3$, and $X^4$ is independently selected from H, F, Cl, or Br;

$R^1$ is H or C(O)-phenyl substituted with one or more of F, Cl, or Br;

$R^4$ is H or alkyl optionally substituted with a hydroxyl or phenyl group; and n is 0 or 1.

2. The compound of claim 1, wherein Z is absent.

3. The compound of claim 1, wherein W is a carboxyl group or an ester group.

4. The compound of claim 3, wherein W is $C(O)-OC_1-C_3$ alkyl.

5. The compound of claim 1, wherein at least one of $X^1$, $X^2$, $X^3$, and $X^4$ is not H or at least one of $X^1$, $X^2$, $X^3$, and $X^4$ is Cl.

6. The compound of claim 1, wherein at least two of $X^2$, $X^3$, and $X^4$ is Cl.

7. The compound of claim 1, wherein each of $X^2$, $X^3$, and $X^4$ is Cl.

8. The compound of claim 1, wherein $R^1$ is H.

9. The compound of claim 1, wherein $R^1$ has the structure of

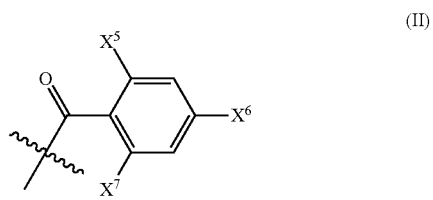

wherein $X^5$, $X^6$, and $X^7$ are independently selected from H, F, Cl, or Br, provided that at least one of $X^5$, $X^6$, and $X^7$ is not H.

10. The compound of claim 9, wherein each of $X^5$, $X^6$, and $X^7$ is Cl.

11. The compound of claim 1, wherein $R^4$ is $C_1$-$C_6$ alkyl optionally substituted with a hydroxyl or phenyl group.

12. The compound of claim 1 and pharmaceutically acceptable salts thereof, wherein the compound is selected from

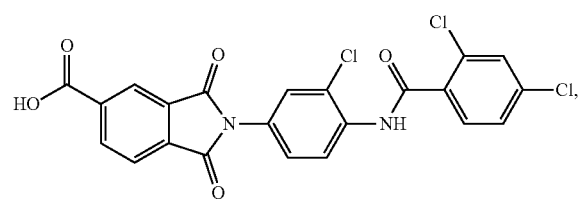
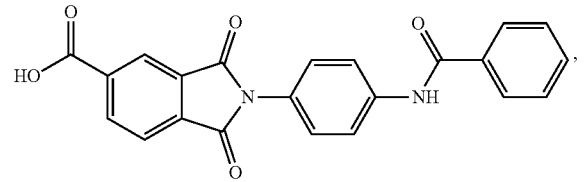
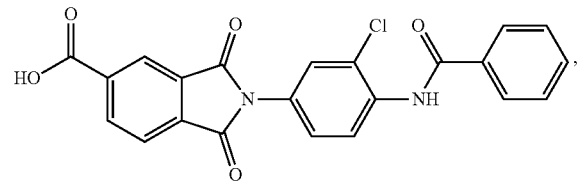
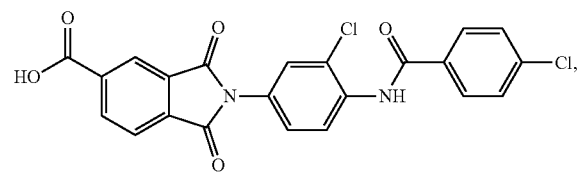
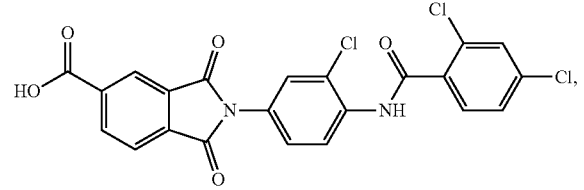
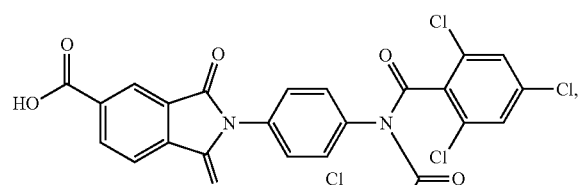
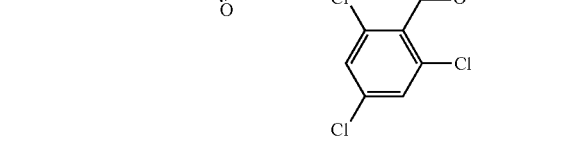
-continued
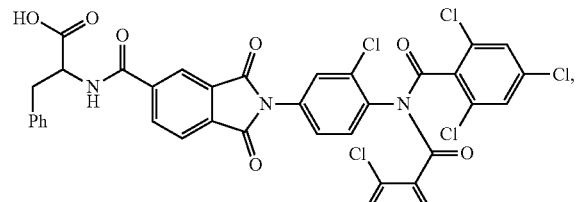
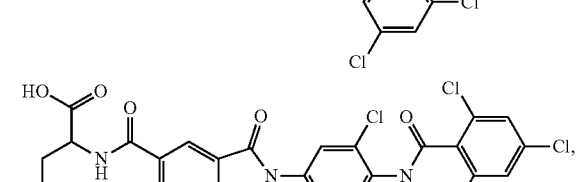
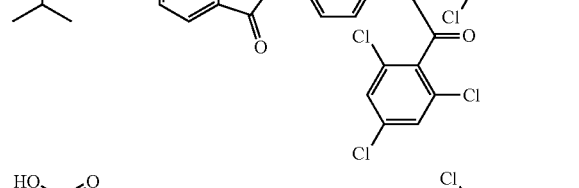
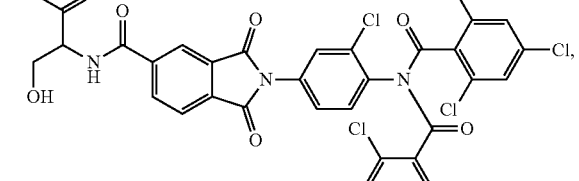
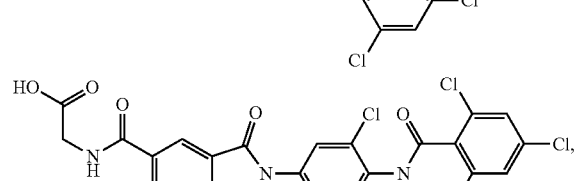
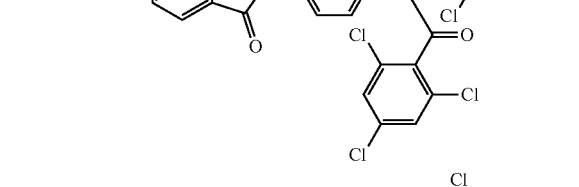
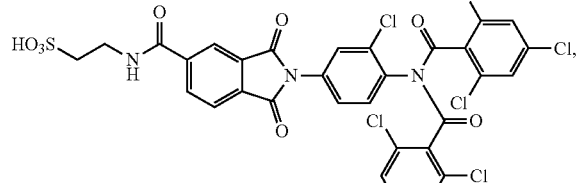
and
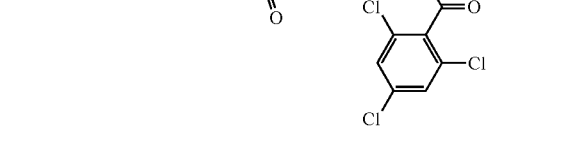

13. The compound of claim 1 and pharmaceutically acceptable salts thereof, wherein the compound has the Formula III,
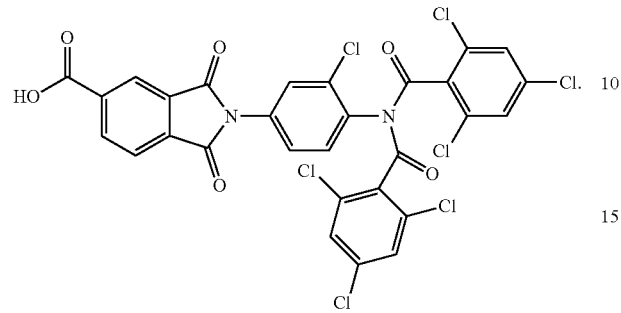
(III)
14. A pharmaceutical composition comprising claim 1 and a pharmaceutically acceptable carrier.
* * * * *